US009669014B2

(12) United States Patent
Siddique et al.

(10) Patent No.: US 9,669,014 B2
(45) Date of Patent: Jun. 6, 2017

(54) SMALL MOLECULE INHIBITORS OF SUPEROXIDE DISMUTASE EXPRESSION

(71) Applicant: Northwestern University, Evanston, IL (US)

(72) Inventors: Teepu Siddique, Wilmette, IL (US); Thomas J. Lukas, Evanston, IL (US); Hasan Arrat, Chicago, IL (US); Gary E. Schiltz, Naperville, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 15/083,848

(22) Filed: Mar. 29, 2016

(65) Prior Publication Data

US 2016/0214969 A1    Jul. 28, 2016

Related U.S. Application Data

(63) Continuation of application No. 14/607,292, filed on Jan. 28, 2015, now abandoned.

(60) Provisional application No. 61/932,509, filed on Jan. 28, 2014.

(51) Int. Cl.
| | | |
|---|---|---|
| *C07D 413/04* | (2006.01) | |
| *A61K 31/4439* | (2006.01) | |
| *C07D 413/14* | (2006.01) | |
| *C07D 271/113* | (2006.01) | |
| *C07D 417/04* | (2006.01) | |
| *C07D 417/14* | (2006.01) | |

(52) U.S. Cl.
CPC ........ *A61K 31/4439* (2013.01); *C07D 413/04* (2013.01); *C07D 271/113* (2013.01); *C07D 413/14* (2013.01); *C07D 417/04* (2013.01); *C07D 417/14* (2013.01)

(58) Field of Classification Search
CPC .......................... A61K 31/4439; C07D 413/04
See application file for complete search history.

(56) References Cited

U.S. PATENT DOCUMENTS 5,527,814 A    6/1996 Louvel

FOREIGN PATENT DOCUMENTS

| DE | WO 2013007663 A1 * | 1/2013 | ........... C07D 413/04 |
|---|---|---|---|
| WO | 2013007663 | 1/2013 | |

OTHER PUBLICATIONS

Koh et al. Experimental Neurology, 2007, 205, 336-346.*
Koh et al. Neurology Research International, 2011, pp. 1-5.*
Ahmad, R.; Iqbal, R.; Akhtar, H.; Zia, u. H.; Duddeck, H.; Stefaniak, L.; Sitkowski, J. Nucleosides Nucleotides Nucleic Acids 2001, 20(9), 1671-1682.
van Es M.; van Vught, P. W.; Van Es, M. A.; Schelhaas, H. J.; van der Kooi, A. J.; de Visser, M.; Veldink, J. H.; van den Berg, L. H. Neurobiol.Aging 2011.
Koh, S. H.; Lee, Y. B.; Kim, K. S.; Kim, H. J.; Kim, M.; Lee, Y. J.; Kim, J.; Lee, K W.; Kim, S. H. Eur.J.Neurosci. 2005, 22(2), 301-309.
Koh, S. H.; Kim, Y.; Kim, H. Y.; Hwang, S.; Lee, C. H.; Kim, S. H. Exp.Neurol. 2007, 205(2), 336-346.
Kurup, A.; Garg, R.; Hansch, C. Chem.Rev. 2001, 101(8), 2573-2600.
Lange, D. J. Pyrimethamine as a therapy for SOD1 associated FALS: Early Findings. Amyotroph. Lateral. Scler. 9 [Suppl. 1], 45-47. 2008.
Leffler, J. E.; Grunwald, E. Rates and Equilibria of Organic Reactions; Wiley: New York, 1963.
Lo, M. F.; Kramer, T.; Gu, J.; Anumala, U. R.; Marinelli, L.; La, P., V; Novellino, E.; Franco, B.; Demedts, D.; van Leuven, F.; Fuertes, A.; Dominguez, J. M.; Plotkin, B.; Eldar-Finkelman, H.; Schmidt, B. J.Med.Chem. 2012, 55(9), 4407-4424.
Maruyama, H.; Morino, H.; Ito, H.; Izumi, Y.; Kato, H.; Watanabe, Y.; Kinoshita, Y.; Kamada, M.; Nodera, H.; Suzuki, H.; Komure, O.; Matsuura, S.; Kobatake, K.; Morimoto, N.; Abe, K.; Suzuki, N.; Aoki, M.; Kawata, A.; Hirai, T.; Kato, T.; Ogasawara, K.; Hirano, A.; Takumi, T.; Kusaka, H.; Hagiwara, K.; Kaji, R.; Kawakami, H. Nature 2010, 465(7295), 223-226.
Matsumoto, S.; Kusaka, H.; Ito, H.; Shibata, N.; Asayama, T.; Imai, T. Clin.Neuropathol. 1996, 15(1), 41-46.
Mettey, Y.; Gompel, M.; Thomas, V.; Garnier, M.; Leost, M.; Ceballos-Picot, I.; Noble, M.; Endicott, J.; Vierfond, J. M.; Meijer, L. J.Med.Chem. 2003, 46(2), 222-236.
Naerum, L.; Norskov-Lauritsen, L.; Olesen, P. H. Bioorg.Med. Chem.Lett. 2002, 12(11), 1525-1528.
Perez, D. I.; Conde, S.; Perez, C.; Gil, C.; Simon, D.; Wandosell, F.; Moreno, F. J.; Gelpi, J. L.; Luque, F. J.; Martinez, A. Bioorg.Med. Chem. 2009, 17(19), 6914-6925.
Rosen, D. R.; Siddique, T.; Patterson, D.; Figlewicz, D. A.; Sapp, P.; Hentati, A.; Donaldson, D.; Goto, J.; O'Regan, J. P.; Deng, H. X.; . Nature 1993, 362(6415), 59-62.
Shi, Y.; Rhodes, N. R.; Abdolvahabi, A.; Kohn, T.; Cook, N. P.; Marti, A. A.; Shaw, B. F. J.Am.Chem.Soc. 2013, in press.
Shibata, N.; Hirano, A.; Kobayashi, M.; Sasaki, S.; Kato, T.; Matsumoto, S.; Shiozawa, Z.; Komori, T.; Ikemoto, A.; Umahara, T.; . Neurosci.Lett. 1994, 179(1-2), 149-152.
Bosco D. A. et al. Wild-type and mutant SOD1 share an aberrant conformation and a common pathogenic pathway in ALS. Nat. Neurosci. 2010, 13(11), 1396-1403.
Broom, W. J. et al. Two approaches to drug discovery in SOD1-mediated ALS. J. Biomol. Screen. 2006, 11(7), 729-735.
Coghlan, M. P. et al. Selective small molecule inhibitors of glycogen synthase kinase-3 modulate glycogen metabolism and gene transcription. Chem. Biol. 2000, 7(10), 793-803.
Dejesus-Hernandez, M. et al. Expanded GGGGCC hexanucleotide repeat in noncoding region of C9ORF72 causes chromosome 9p-linked FTD and ALS. Neuron 2011.

(Continued)

*Primary Examiner* — Matthew Coughlin
(74) *Attorney, Agent, or Firm* — Andrus Intellectual Property Law, LLP

(57) ABSTRACT

Disclosed are new small molecules and the uses thereof for inhibiting superoxide dismutase (SOD) expression. Also disclosed are pharmaceutical compositions comprising the small molecule inhibitors which may be administered in methods of treating diseases or disorders associated with elevated SOD expression or activity, including neurological diseases and disorders such as amyotrophic lateral sclerosis (ALS).

8 Claims, 7 Drawing Sheets

(56) References Cited

OTHER PUBLICATIONS

Deng, H. X. et al. Transgenic mouse models and human neurodegenerative disorders. 2000, 57(12), 1695-1702.
Deng, H. X. et al. FUS-immunoreactive inclusions are a common feature in sporadic and non-SOD1 familial amyotrophic lateral sclerosis. Ann. Neurol. 2010, 67(6), 739-748.
Deng, H. X. et al. Mutations in UBQLN2 cause dominant X-linked juvenile and adult-onset ALS and ALS/dementia. Nature 2011, 477(7363), 211-215.
Forsberg, K. et al. Novel antibodies reveal inclusions containing non-native SOD1 in sporadic ALS patients. PLoS. One. 2010, 5(7), e11552.
Systemfit: A Package for Estimating Systems of Simultaneous Equations in R. Journal of Statistical Software. 2007, 23(4), 1-40.
Kabashi, E. et al. Gain and loss of function of ALS-related mutations of TARDBP (TDP-43) cause motor deficits in vivo. Hum. Mol. Genet. 2010, 19(4), 671-683.
Kwiatkowski, T. J. et al. Mutations in the FUS/TLS gene on chromosome 16 cause familial amyotrophic lateral sclerosis. Science. 2009, 323(5918), 1205-1208.
Leost, M. et al. Paullones are potent inhibitors of glycogen synthase kinase-3beta and cyclin-dependent kinase 5/p25. Eur. J. Biochem. 2000, 267(19), 5983-5994.
Mackenzie, I. R. et al. Pathological TDP-43 distinguishes sporadic amyotrophic lateral sclerosis from amyotrophic lateral sclerosis with SOD1 mutations. Ann. Neurol. 2007, 61(5), 427-434.
Min, W. W. et al. Elevated glycogen synthase kinase-3 activity in Fragile X mice: key metabolic regulator with evidence for treatment potential. Neuropharmacology. 2009, 56(2), 463-472.
Ralph, G. S. et al. Silencing mutant SOD1 using RNAi protects against neurodegeneration and extends survival in an ALS model. Nat. Med. 2005, 11(4), 429-433.
Renton, A. E. et al. A hexanucleotide repeat expansion in C9ORF72 is the cause of chromosome 9p21-linked ALS-FTD. Neuron. 2011.
Smith, R. A. et al. Antisense oligonucleotide therapy for neurodegenerative disease. J. Clin. Invest. 2006, 116(8), 2290-2296.
Sreedharan, J. et al. TDP-43 mutations in familial and sporadic amyotrophic lateral sclerosis. Science. 2008, 319(5870), 1668-1672.
Valerio, A. et al. Glycogen synthase kinase-3 inhibition reduces ischemic cerebral damage, restores impaired mitochondrial biogenesis and prevents ROS production. J. Neurochem. 2011, 116(6), 1148-1159.
Vance, C. et al. Mutations in FUS, an RNA processing protein, cause familial amyotrophic lateral sclerosis type 6. Science. 2009, 323(5918), 1208-1211.
Wang, L. et al. Mutant SOD1 knockdown in all cell types ameliorates disease in G85R SOD1 mice with a limited additional effect over knockdown restricted to motor neurons. J. Neurochem. 2010, 113(1), 166-174.
Williams, H.D. et al. Strategies to address low drug solubility in discovery and development. J. Pharmacol. Rev. 2013, 65(1), 315-499.
Wright, P.D. et al. Screening for inhibitors of the SOD1 gene promoter: pyrimethamine does not reduce SOD1 levels in cell and animal models. Neurosci. Lett. 2010, 482, 188-192.
Yang, Y. M. et al. A small molecule screen in stem-cell-derived motor neurons identities a kinase inhibitor as a candidate therapeutic for ALS. Cell stem Cell. 2013, 12(6), 713-726.
Zetterstrom, P. et al. Misfolded superoxide dismutase-1 in CSF from amyotrophic lateral sclerosis patients. J. Neurochem. 2011, 117(1), 91-99.
Zhong, Z. et al. Activated protein C therapy slows ALS-like disease in mice by transcriptionally inhibiting SOD1 in motor neurons and microglia cells. J. Clin. Invest. 2009, 119(11), 3437-3449.

\* cited by examiner

NUCC-322

NUCC-437

NUCC-438

SMALL MOLECULE INHIBITORS OF SUPEROXIDE DISMUTASE EXPRESSION

CROSS-REFERENCE TO RELATED PATENT APPLICATIONS

The present application is a continuation of U.S. application Ser. No. 14/607,292, filed on Jan. 28, 2015, which application was published on Jul. 30, 2015, as US2015/0210679, which application further claims the benefit under 35 U.S.C. §119(e) to U.S. Provisional Patent Application No. 61/932,509, filed on Jan. 28, 2014, the contents of which are incorporated herein by reference in their entireties.

BACKGROUND

The field of the invention relates to new small molecules and uses of the small molecules for inhibiting expression of superoxide dismutase (SOD) and treating diseases and disorders characterized by aberrant SOD activity or expression. Superoxide dismutases (SOD)(EC 1.15.1.1) are enzymes that catalyze the dismutation of dioxide radicals ($O_2^-$) into oxide and hydrogen peroxide. As such, SODs provide an antioxidant defense in cells exposed to oxygen. Three forms of SODs are found in humans and in other mammals: SOD1, which is cytoplasmic; SOD2, which is mitochondrial; and SOD3, which is extracellular. SOD1 and SOD3 contain copper (Cu) and Zinc (Zn) in their reactive centers and are sometimes referred to as Cu,Zn-SODs. SOD2 contains manganese (Mn) in its reactive center and sometimes is referred to as Mn-SOD.

The SOD family of enzymes have been linked to a variety of diseases and disorders. (See, e.g., Noor et al., Med. Sci. Monit. 2002; 8(9):RA210-215; and Macmillan-Crow et al., Free Radic. Res. 2001 April; 34(4):325-36; the contents of which are incorporated herein by reference in their entireties). In particular, mutations in the SOD1 gene have been linked with familial amyotrophic lateral sclerosis (ALS), which is a degenerative motor neuron disease. Some mutations in SOD1 induce a toxic gain of function that is associated with the formation of protein aggregates as in ALS. (See, e.g., Milani et al. (2011) Neurol Res Int. 2011: 458427. doi:10.1155/2011/458427; Deng et al., (August 1993) Science. 261 (5124): 1047-51; Conwit R A (December 2006) J. Neurol. Sci. 251 (1-2): 1-2; and Leigh et al. (August 2000), Current Opinion in Neurology 13 (4): 397-405. doi:10.1097/00019052-200008000-00006; the contents of which are incorporated herein by reference in their entireties). Because some mutant forms of SOD1 induce a toxic gain of function associated with formation of protein aggregates in ALS, inhibition of expression of these mutant forms of SOD1 for treating ALS currently is a pharmacological target in current clinical trials. (See Lange, Amyotrophic. Lateral. Scler. 9[Suppl. 1], 45-47, 2008; and Smith et al., J. Clin. Invest. 116, 2290-2296, 2006). However, some inhibitors of SOD1 expression exhibit cell toxicity at effective concentrations and new inhibitors of SOD1 expression are desirable, in particular, small molecule inhibitors of superoxide dismutase expression.

SUMMARY

Disclosed are new small molecules and uses thereof for inhibiting superoxide dismutase (SOD) expression. Also disclosed are pharmaceutical compositions that comprise the small molecules. The small molecule may inhibit superoxide dismutase expression by inhibiting glycogen synthase kinase III activity or inhibiting the activity of other protein kinase activities. Also disclosed are methods of treating diseases or disorders associated with aberrant SOD activity or expression, including neurological diseases and disorders such as amyotrophic lateral sclerosis (ALS).

The small molecules disclosed herein may include 1,3,4-oxidiazole or 1,3,4-thiadiazole compounds. In some embodiments, the compounds may include compounds or salts, esters, amides, or solvates thereof having a Formula I:

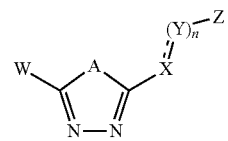

where A is O or S. In Formula I, preferably, W is a saturated or unsaturated homocycle or heterocycle comprising or consisting of one 5- or 6-membered ring or two fused 5- or 6-membered rings, and W is optionally substituted at one or more positions with an amino group, a 4-fluorophenyl group, a hydroxyl group, an anilino group, a benzylamino group, or a tetrahydropuro-4-amino group. In Formula I, preferably Z is C1-C6 alkyl or a saturated or unsaturated homocycle or heterocycle comprising or consisting of one 5- or 6-membered ring or two fused 5- or 6-membered rings, and Z is optionally substituted at one or more positions with a C1-6 alkyl group, a C1-6 alkoxy group, a halo group, an haloalkyl group, a cyano group, a nitro group, a 2-morpholino-ethoxy group, a phenyl group, a halophenyl group, a phenoxy group, an oxo group, a phenylamino group, a benzylamino group, a tetrahydropuran-4-methoxy group, or a 2-dimethylamino-ethoxy group. In Formula I, preferably X is S, S(O), S(OXO), O, NH, CH, or $CH_2$. In Formula I, preferably Y is CH or $CH_2$ and n is 0, 1, or 2.

In some embodiments, the disclosed 1,3,4-oxidiazole or 1,3,4-thiadiazole compounds may have Formula I where W is selected from the group consisting of:

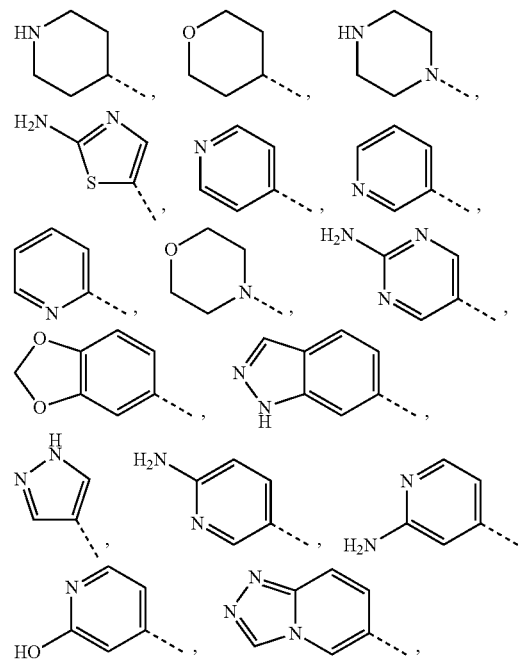

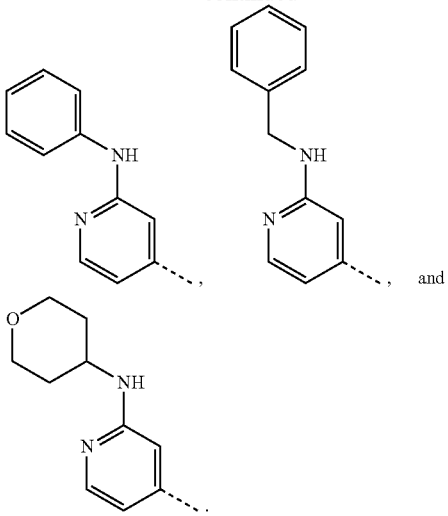

In further embodiments, the disclosed 1,3,4-oxidiazole or 1,3,4-thiadiazole compounds may have Formula I where W is selected from the group consisting of:

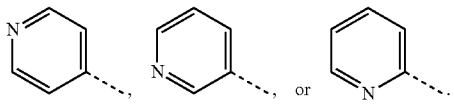

In some embodiments, the 1,3,4-oxidiazole or 1,3,4-thiadiazole compounds may have Formula I where Z is phenyl substituted at one or more positions with C1-C6 alkoxy or halogen. For example, in some embodiments Z may be selected from the group consisting of:

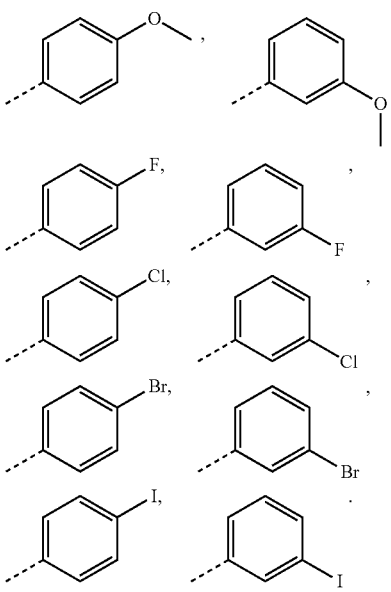

In even further embodiments, the 1,3,4-oxidiazole or 1,3,4-thiadiazole compounds may have Formula I where Z may be selected from the group consisting of:

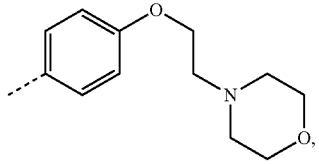
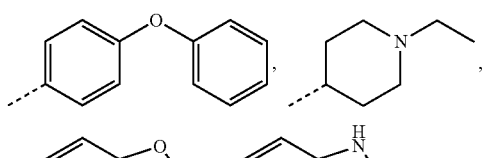
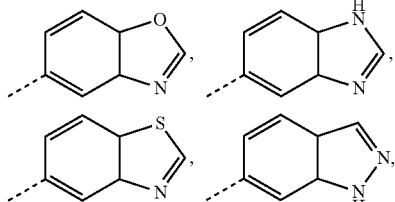
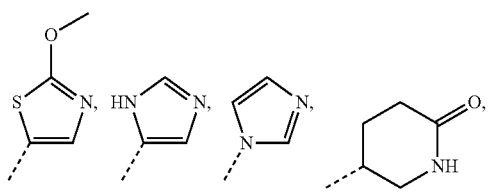
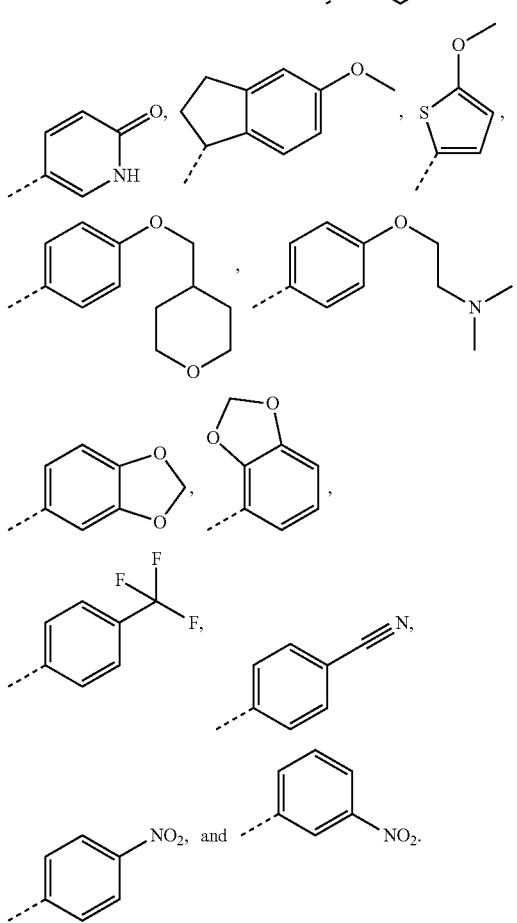

Specifically disclosed 1,3,4-oxidiazole or 1,3,4-thiadiazole compounds may include but are not limited to the following compounds:

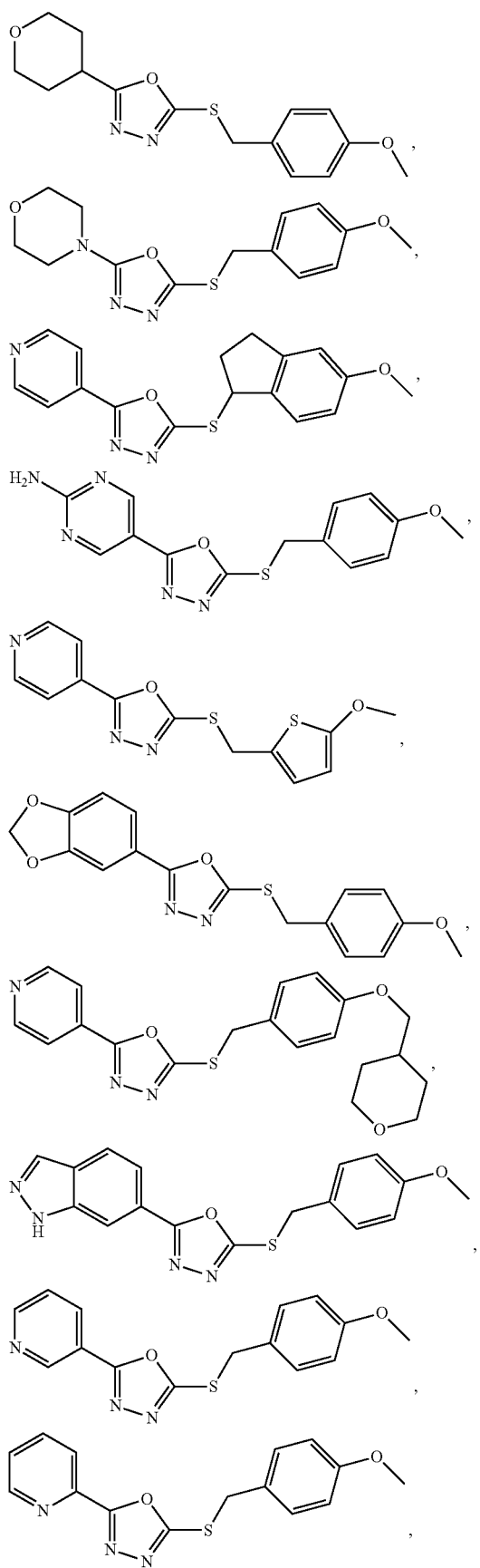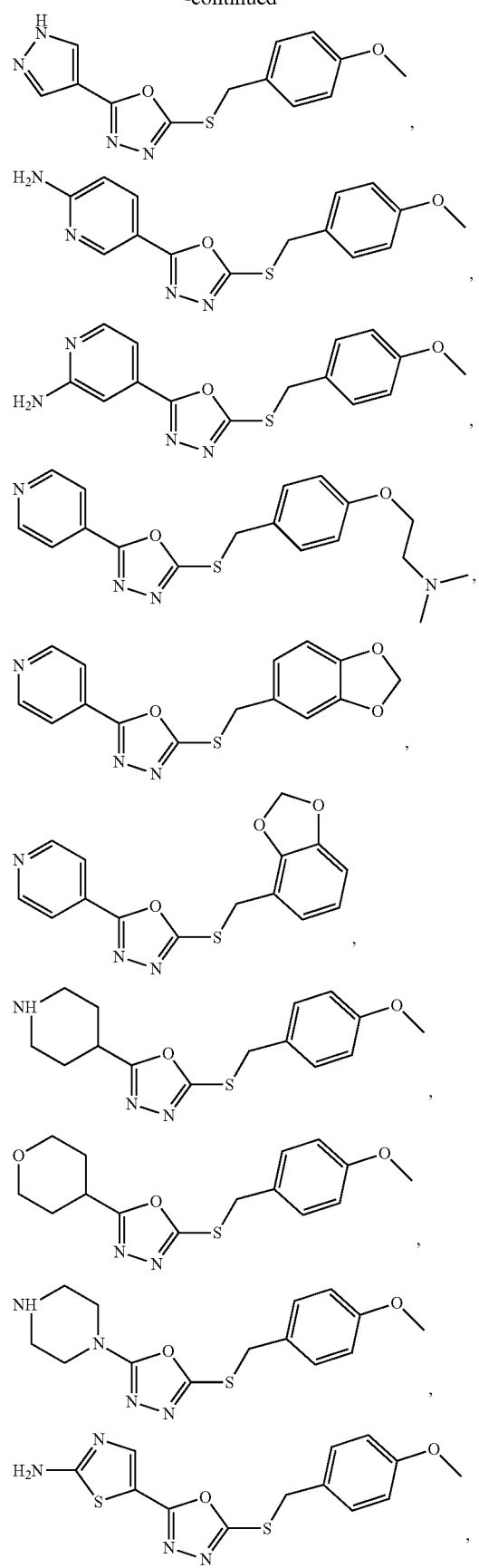

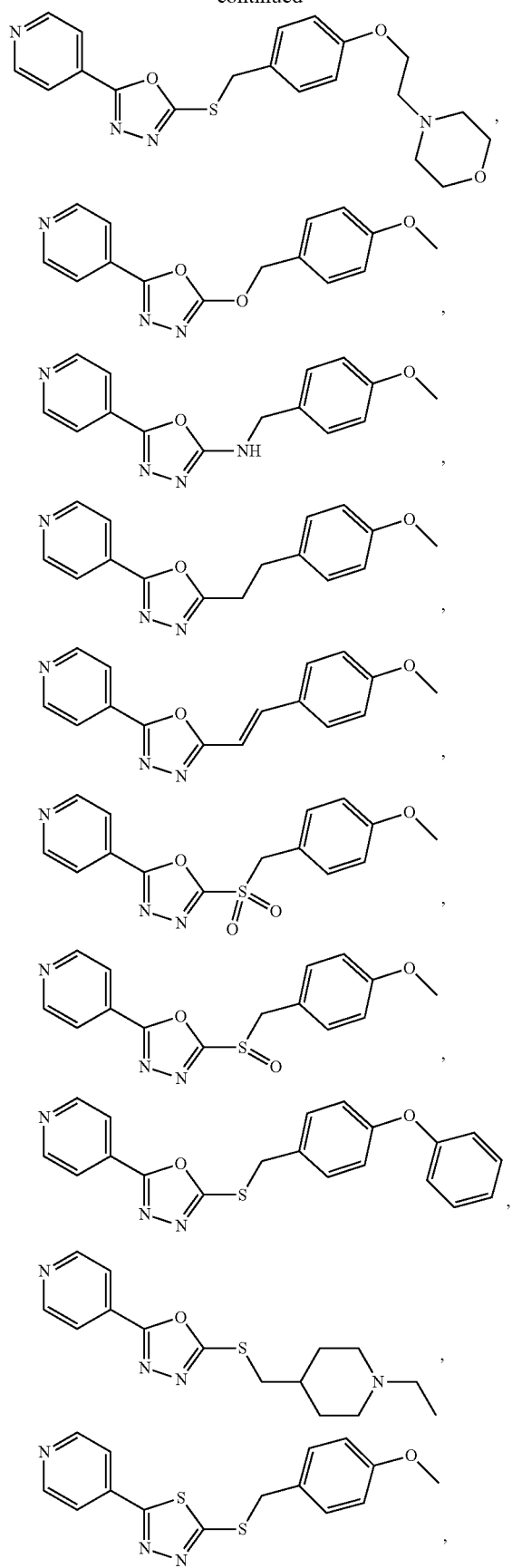
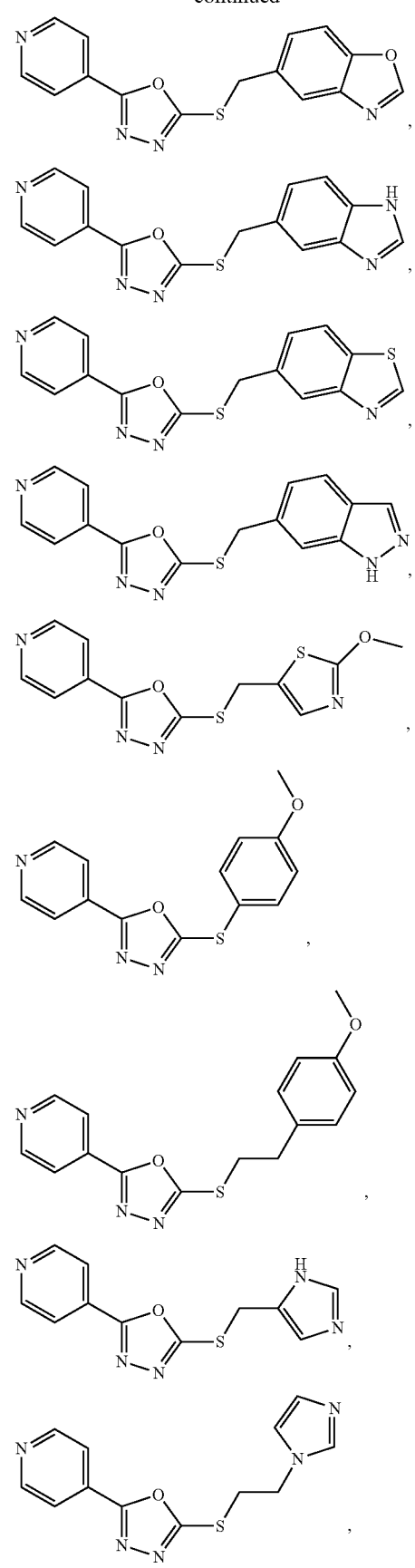

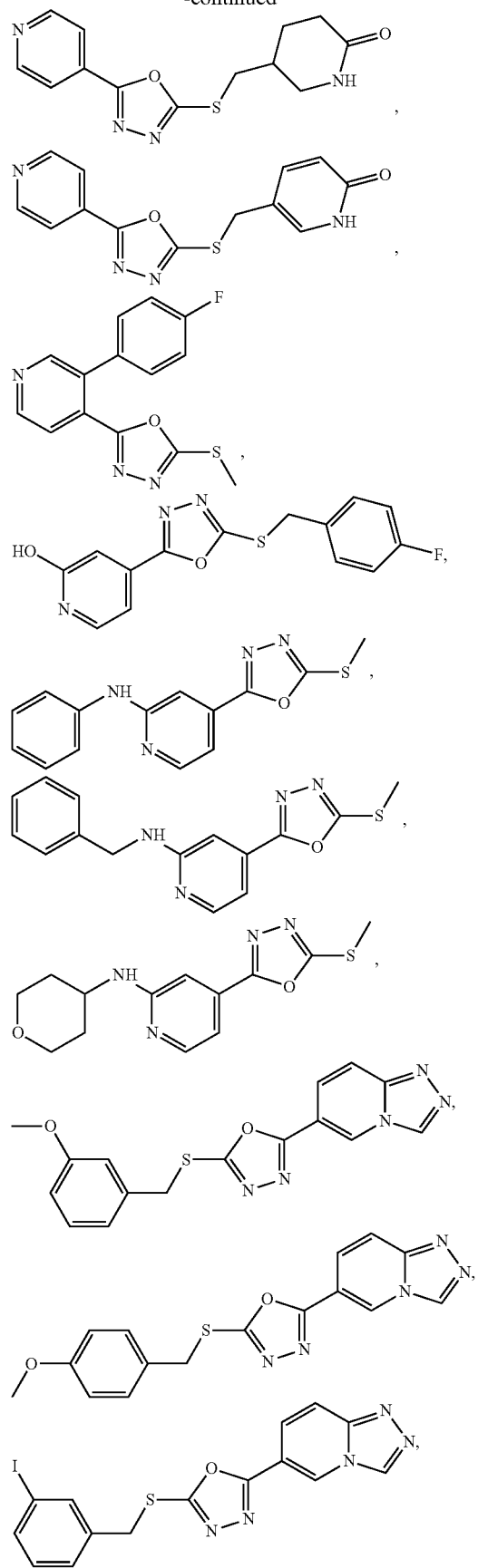
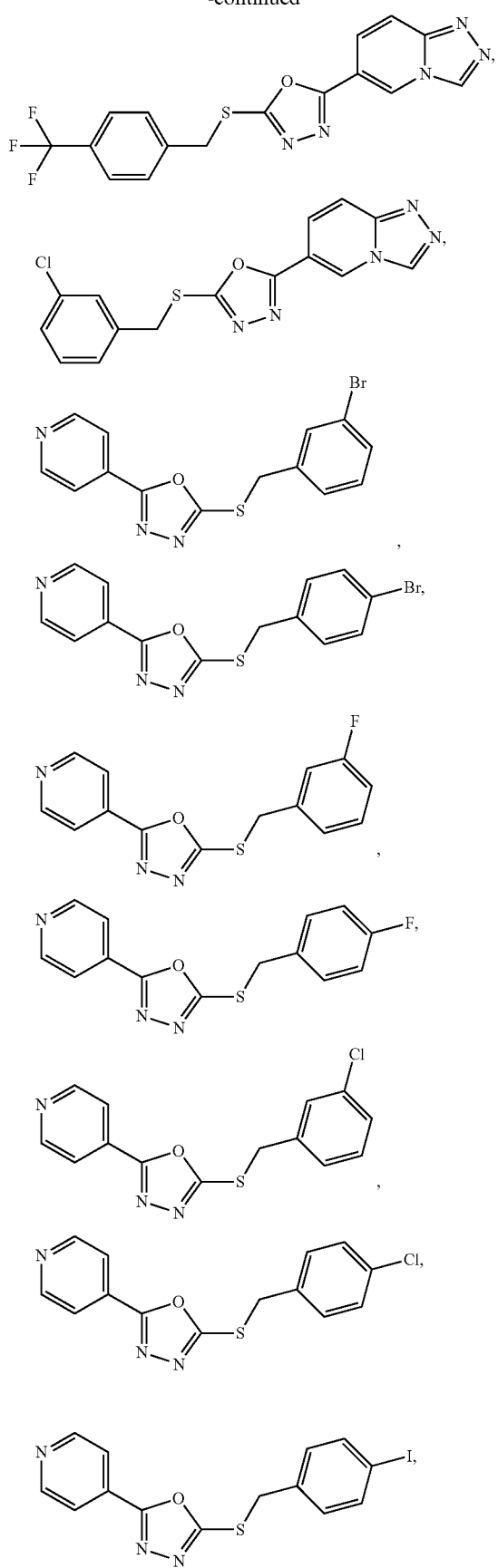

-continued
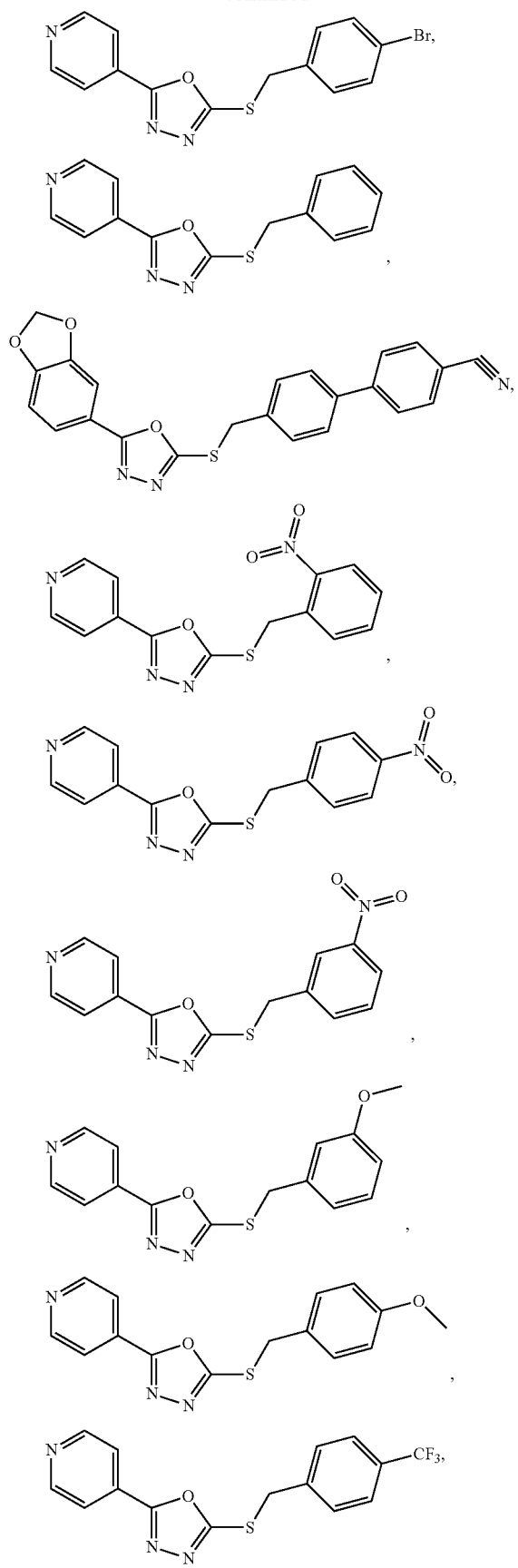
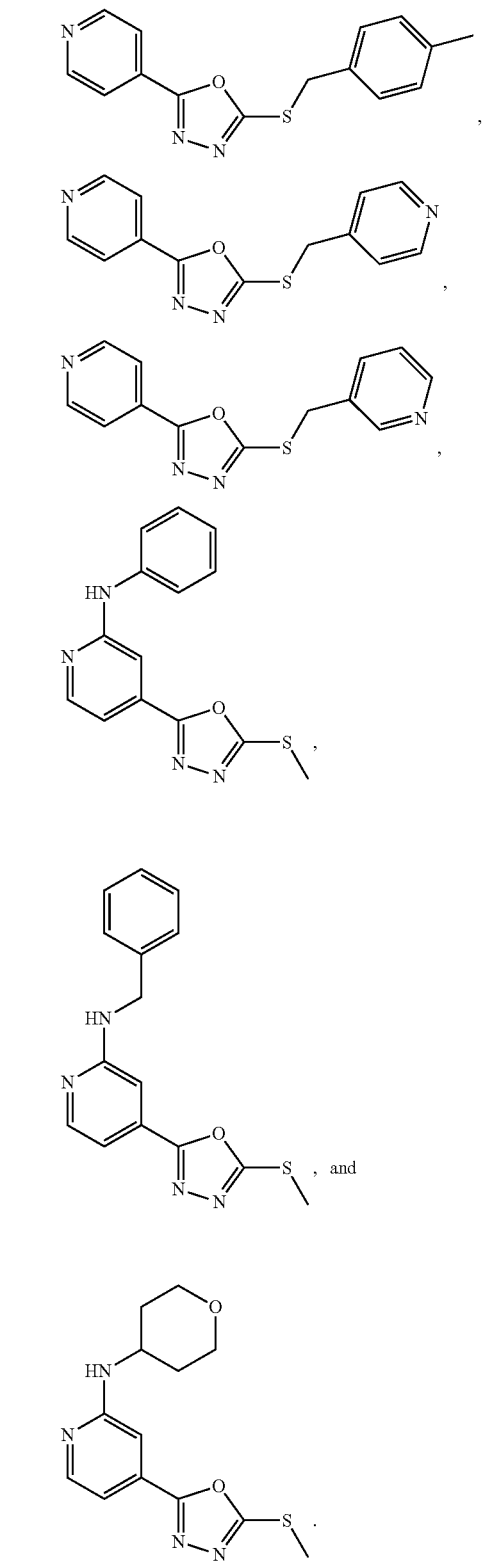
Other examples of small molecule disclosed herein may include compounds that are not 1,3,4-oxidiazole or 1,3,4-thiadiazole compounds. For example, other examples of the small molecules disclosed herein may include but are not limited to compounds having the following formulae:

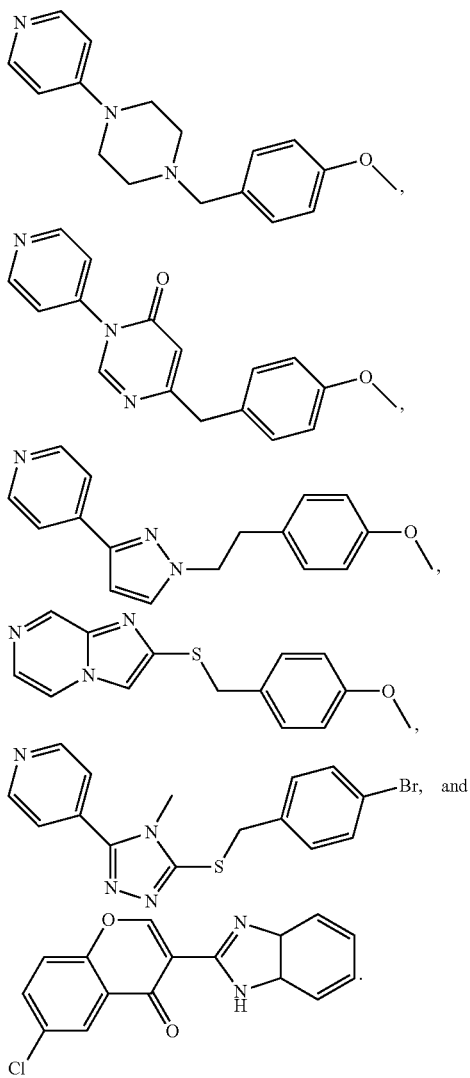

The presently disclosed small molecules preferably inhibit expression of superoxide dismutase. Small molecule inhibitors of superoxide dismutase expression may be formulated as pharmaceutical compositions. In some embodiments, small molecule inhibitors of superoxide dismutase expression may be formulated as pharmaceutical compositions and administered to a patient to treat a disease or disorder associated with aberrant superoxide dismutase expression or activity. Suitable diseases or disorders treated by the disclosed pharmaceutical compositions may include but are not limited to neurological diseases and disorders. Suitable neurological diseases and disorders treated by the disclosed pharmaceutical compositions may include, but are not limited to degenerative neurological diseases or disorders such as amyotrophic lateral sclerosis (ALS).

DETAILED DESCRIPTION

Figure 1:
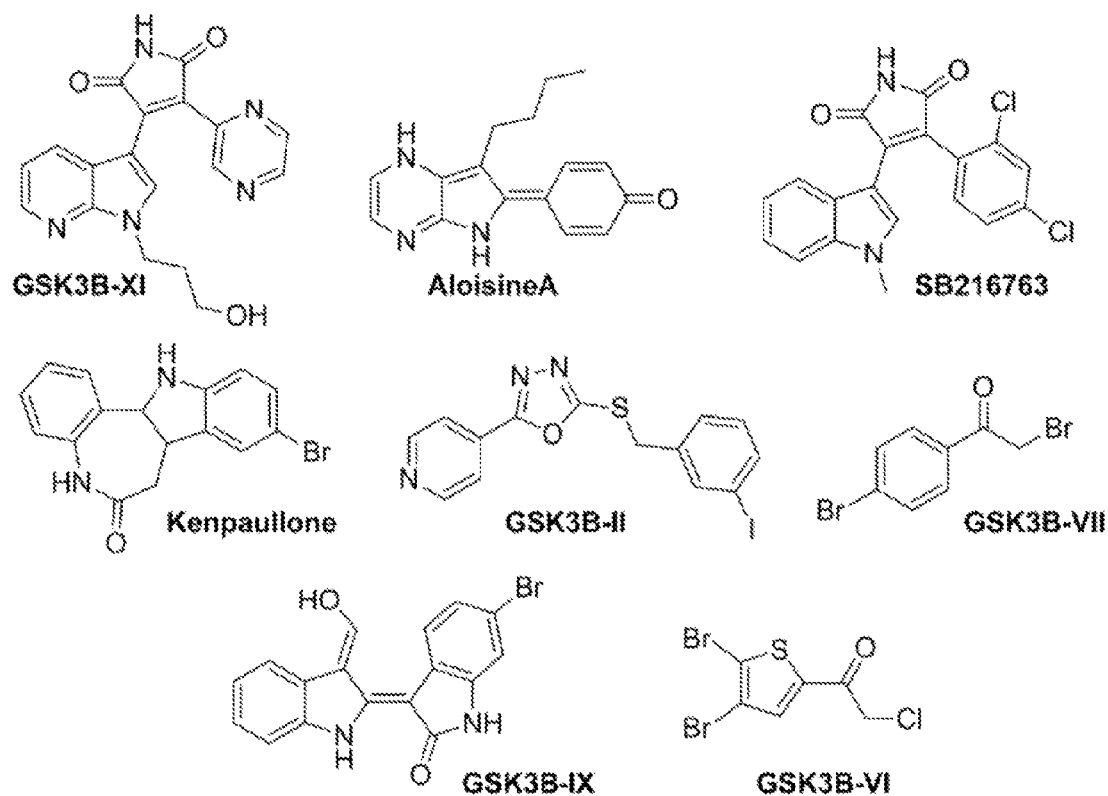
FIG. 1. Chemical structures of the commercially available compounds tested in the in vitro assays for their ability to inhibit SOD1.

The disclosed subject matter further may be described utilizing terms as defined below.

Unless otherwise specified or indicated by context, the terms "a", "an", and "the" mean "one or more." For example, "an inhibitor of superoxide dismutase expression" should be interpreted to mean "one or more inhibitors of superoxide dismutase expression."

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion additional components other than the components recited in the claims. The term "consisting essentially of" should be interpreted to be partially closed and allowing the inclusion only of additional components that do not fundamentally alter the nature of the claimed subject matter.

The terms "patient" and "subject" may be used interchangeably herein. A patient may be a human patient. A patient may refer to a human patient having or at risk for acquiring a disease or disorder that is associated with aberrant superoxide dismutase (SOD) expression or activity. As used herein, the term "aberrant" means higher or lower expression or activity, typically higher expression or activity, relative to a normal healthy patient. A patient may refer to a human patient having or at risk for acquiring a disease or disorder that is associated with elevated expression or activity of Cu,Zn-superoxide dismutase, otherwise referred to as "SOD1." In some embodiments, a patient may have a mutant form of the gene encoding SOD1 which results in elevated expression or activity of SOD1, in which case, the patient may be treated by inhibiting expression of the mutant form of SOD1 by administering the presently disclosed small molecule inhibitors of SOD1 expression. In specific embodiments, a patient may refer to a human patient having or at risk for acquiring a neurological disease or disorder, including degenerative neurological diseases or disorders such as amyotrophic lateral sclerosis (ALS) associated with aberrant SOD1 expression or activity.

The compounds disclosed herein preferably inhibit expression of superoxide dismutase, including expression of SOD1. Inhibition of expression of superoxide dismutase may be assessed utilizing methods known in the art and the methods disclosed herein, including the methods disclosed in the Examples provided herein. In some embodiments, the compounds inhibit expression of superoxide dismutase relative to a control (e.g., by at least about 10%, 20%, 30%, 40%, 50%, 60%, 70%, 80%, 90%, or more). In other embodiments, an IC50 value for the compound in regard to inhibition of superoxide dismutase expression may be determined and preferably the compound has an IC50 value of less than about 10 µM, 5 µM, or 1 µM.

The compounds disclosed herein optionally may inhibit glycogen synthase kinase III activity or other protein kinase activities. Inhibition of glycogen synthase kinase III activity may be assessed utilizing methods known in the art and the methods disclosed herein, including the methods disclosed in the Examples provided herein. In some embodiments, an IC50 value for the compound may be determined in regard to inhibition of glycogen synthase kinase III activity or inhibition of other protein kinase activities and preferably the compound has an IC50 value of less than about 1000 nM, 500 nM, or 100 nM.

The compounds disclosed herein may include 1,3,4-oxidiazole or 1,3,4-thiadiazole compounds, which may be synthesized utilizing methods known in the art and methods disclosed herein, including the methods disclosed in the Examples provided herein. (See e.g., Ahman, R. et al., J. Nucleosides Nucleotides Nucleic Acids 2001 20(9), 1671-1682; and Lo et al., J. Med. Chem. 2012, 55(9), 4407-4424, the contents of which are incorporated herein by reference in their entireties).

The compounds disclosed herein (e.g., compounds of Formula I) may have several chiral centers, and stereoisomers, epimers, and enantiomers are contemplated. The compounds may be optically pure with respect to one or more chiral centers (e.g., some or all of the chiral centers may be completely in the S configuration; some or all of the chiral centers may be completely in the R configuration; etc.). Additionally or alternatively, one or more of the chiral centers may be present as a mixture of configurations (e.g., a racemic or another mixture of the R configuration and the S configuration). Compositions comprising substantially purified stereoisomers, epimers, or enantiomers, or analogs or derivatives thereof are contemplated herein (e.g., a composition comprising at least about 90%, 95%, or 99%0 pure stereoisomer, epimer, or enantiomer.) As used herein, formulae which do not specify the orientation at one or more chiral centers are meant to encompass all orientations and mixtures thereof.

The compounds employed in the compositions and methods disclosed herein may be administered as pharmaceutical compositions and, therefore, pharmaceutical compositions incorporating the compounds are considered to be embodiments of the compositions disclosed herein. Such compositions may take any physical form which is pharmaceutically acceptable; illustratively, they can be orally administered pharmaceutical compositions. Such pharmaceutical compositions contain an effective amount of a disclosed compound, which effective amount is related to the daily dose of the compound to be administered. Each dosage unit may contain the daily dose of a given compound or each dosage unit may contain a fraction of the daily dose, such as one-half or one-third of the dose. The amount of each compound to be contained in each dosage unit can depend, in part, on the identity of the particular compound chosen for the therapy and other factors, such as the indication for which it is given. The pharmaceutical compositions disclosed herein may be formulated so as to provide quick, sustained, or delayed release of the active ingredient after administration to the patient by employing well known procedures.

The compounds for use according to the methods of disclosed herein may be administered as a single compound or a combination of compounds. For example, a compound that inhibits SOD1 expression may be administered as a single compound or in combination with another compound that inhibits SOD1 expression or that has a different pharmacological activity.

As indicated above, pharmaceutically acceptable salts of the compounds are contemplated and also may be utilized in the disclosed methods. The term "pharmaceutically acceptable salt" as used herein, refers to salts of the compounds which are substantially non-toxic to living organisms. Typical pharmaceutically acceptable salts include those salts prepared by reaction of the compounds as disclosed herein with a pharmaceutically acceptable mineral or organic acid or an organic or inorganic base. Such salts are known as acid addition and base addition salts. It will be appreciated by the skilled reader that most or all of the compounds as disclosed herein are capable of forming salts and that the salt forms of pharmaceuticals are commonly used, often because they are more readily crystallized and purified than are the free acids or bases.

Acids commonly employed to form acid addition salts may include inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of suitable pharmaceutically acceptable salts may include the sulfate, pyrosulfate, bisulfate, sulfite, bisulfate, phosphate, monohydrogenphosphate, dihydrogenphosphate, metaphosphate, pyrophosphate, bromide, iodide, acetate, propionate, decanoate, caprylate, acrylate, formate, hydrochloride, dihydrochloride, isobutyrate, caproate, heptanoate, propiolate, oxalate, malonate, succinate, suberate, sebacate, fumarate, maleat-, butyne-.1,4-dioate, hexyne-1,6-dioate, benzoate, chlorobenzoate, methylbenzoate, hydroxybenzoate, methoxybenzoate, phthalate, xylenesulfonate, phenylacetate, phenylpropionate, phenylbutyrate, citrate, lactate, alpha-hydroxybutyrate, glycolate, tartrate, methanesulfonate, propanesulfonate, naphthalene-1-sulfonate, naphthalene-2-sulfonate, mandelate, and the like.

Base addition salts include those derived from inorganic bases, such as ammonium or alkali or alkaline earth metal hydroxides, carbonates, bicarbonates, and the like. Bases useful in preparing such salts include sodium hydroxide, potassium hydroxide, ammonium hydroxide, potassium carbonate, sodium carbonate, sodium bicarbonate, potassium bicarbonate, calcium hydroxide, calcium carbonate, and the like.

The particular counter-ion forming a part of any salt of a compound disclosed herein is may not be critical to the activity of the compound, so long as the salt as a whole is pharmacologically acceptable and as long as the counterion does not contribute undesired qualities to the salt as a whole. Undesired qualities may include undesirably solubility or toxicity.

Pharmaceutically acceptable esters and amides of the compounds can also be employed in the compositions and methods disclosed herein. Examples of suitable esters include alkyl, aryl, and aralkyl esters, such as methyl esters, ethyl esters, propyl esters, dodecyl esters, benzyl esters, and the like. Examples of suitable amides include unsubstituted amides, monosubstituted amides, and disubstituted amides, such as methyl amide, dimethyl amide, methyl ethyl amide, and the like.

In addition, the methods disclosed herein may be practiced using solvate forms of the compounds or salts, esters, and/or amides, thereof. Solvate forms may include ethanol solvates, hydrates, and the like.

The pharmaceutical compositions may be utilized in methods of treating a disease or disorder associated with superoxide dismutase mutations, including SOD1. For example, the pharmaceutical compositions may be utilized to treat patients having or at risk for acquiring a neurological disease or disorder, including degenerative neurological diseases or disorders such as ALS. Suitable patients include, for example mammals, such as humans and non-human primates (e.g., chimps) or other mammals (e.g., dogs, cats, horses, rats, and mice). Suitable human patients may include, for example, those who have previously been determined to be at risk of having or developing a neurological disease or disorder, including degenerative neurological diseases or disorders such as ALS.

As used herein, the terms "treating" or "to treat" each mean to alleviate symptoms, eliminate the causation of resultant symptoms either on a temporary or permanent basis, and/or to prevent or slow the appearance or to reverse the progression or severity of resultant symptoms of the named disease or disorder. As such, the methods disclosed herein encompass both therapeutic and prophylactic administration.

As used herein the term "effective amount" refers to the amount or dose of the compound, upon single or multiple dose administration to the subject, which provides the desired effect in the subject under diagnosis or treatment. The disclosed methods may include administering an effective amount of the disclosed compounds (e.g., as present in a pharmaceutical composition) for treating a disease or disorder associated with superoxide dismutase mutations, including administering an effective amount of a compound that inhibits expression of the mutated form of superoxide dismutase.

An effective amount can be readily determined by the attending diagnostician, as one skilled in the art, by the use of known techniques and by observing results obtained under analogous circumstances. In determining the effective amount or dose of compound administered, a number of factors can be considered by the attending diagnostician, such as: the species of the subject; its size, age, and general health; the degree of involvement or the severity of the disease or disorder involved; the response of the individual subject; the particular compound administered; the mode of administration; the bioavailability characteristics of the preparation administered; the dose regimen selected; the use of concomitant medication; and other relevant circumstances.

A typical daily dose may contain from about 0.01 mg/kg to about 100 mg/kg (such as from about 0.05 mg/kg to about 50 mg/kg and/or from about 0.1 mg/kg to about 25 mg/kg) of each compound used in the present method of treatment.

Compositions can be formulated in a unit dosage form, each dosage containing from about 1 to about 500 mg of each compound individually or in a single unit dosage form, such as from about 5 to about 300 mg, from about 10 to about 100 mg, and/or about 25 mg. The term "unit dosage form" refers to a physically discrete unit suitable as unitary dosages for a patient, each unit containing a predetermined quantity of active material calculated to produce the desired therapeutic effect, in association with a suitable pharmaceutical carrier, diluent, or excipient.

Oral administration is an illustrative route of administering the compounds employed in the compositions and methods disclosed herein. Other illustrative routes of administration include transdermal, percutaneous, intravenous, intramuscular, intranasal, buccal, intrathecal, intracerebral, or intrarectal routes. The route of administration may be varied in any way, limited by the physical properties of the compounds being employed and the convenience of the subject and the caregiver.

As one skilled in the art will appreciate, suitable formulations include those that are suitable for more than one route of administration. For example, the formulation can be one that is suitable for both intrathecal and intracerebral administration. Alternatively, suitable formulations include those that are suitable for only one route of administration as well as those that are suitable for one or more routes of administration, but not suitable for one or more other routes of administration. For example, the formulation can be one that is suitable for oral, transdermal, percutaneous, intravenous, intramuscular, intranasal, buccal, and/or intrathecal administration but not suitable for intracerebral administration.

The inert ingredients and manner of formulation of the pharmaceutical compositions are conventional. The usual methods of formulation used in pharmaceutical science may be used here. All of the usual types of compositions may be used, including tablets, chewable tablets, capsules, solutions, parenteral solutions, intranasal sprays or powders, troches, suppositories, transdermal patches, and suspensions. In general, compositions contain from about 0.5% to about 50% of the compound in total, depending on the desired doses and the type of composition to be used. The amount of the compound, however, is best defined as the "effective amount", that is, the amount of the compound which provides the desired dose to the patient in need of such treatment. The activity of the compounds employed in the compositions and methods disclosed herein are not believed to depend greatly on the nature of the composition, and, therefore, the compositions can be chosen and formulated primarily or solely for convenience and economy.

Capsules are prepared by mixing the compound with a suitable diluent and filling the proper amount of the mixture in capsules. The usual diluents include inert powdered substances (such as starches), powdered cellulose (especially crystalline and microcrystalline cellulose), sugars (such as fructose, mannitol and sucrose), grain flours, and similar edible powders.

Tablets are prepared by direct compression, by wet granulation, or by dry granulation. Their formulations usually incorporate diluents, binders, lubricants, and disintegrators (in addition to the compounds). Typical diluents include, for example, various types of starch, lactose, mannitol, kaolin, calcium phosphate or sulfate, inorganic salts (such as sodium chloride), and powdered sugar. Powdered cellulose derivatives can also be used. Typical tablet binders include substances such as starch, gelatin, and sugars (e.g., lactose, fructose, glucose, and the like). Natural and synthetic gums can also be used, including acacia, alginates, methylcellulose, polyvinylpyrrolidine, and the like. Polyethylene glycol, ethylcellulose, and waxes can also serve as binders.

Tablets can be coated with sugar, e.g., as a flavor enhancer and sealant. The compounds also may be formulated as chewable tablets, by using large amounts of pleasant-tasting substances, such as mannitol, in the formulation. Instantly dissolving tablet-like formulations can also be employed, for example, to assure that the patient consumes the dosage form and to avoid the difficulty that some patients experience in swallowing solid objects.

A lubricant can be used in the tablet formulation to prevent the tablet and punches from sticking in the die. The lubricant can be chosen from such slippery solids as talc, magnesium and calcium stearate, stearic acid, and hydrogenated vegetable oils.

Tablets can also contain disintegrators. Disintegrators are substances that swell when wetted to break up the tablet and release the compound. They include starches, clays, celluloses, algins, and gums. As further illustration, corn and potato starches, methylcellulose, agar, bentonite, wood cellulose, powdered natural sponge, cation-exchange resins, alginic acid, guar gum, citrus pulp, sodium lauryl sulfate, and carboxymethylcellulose can be used.

Compositions can be formulated as enteric formulations, for example, to protect the active ingredient from the strongly acid contents of the stomach. Such formulations can be created by coating a solid dosage form with a film of a polymer which is insoluble in acid environments and soluble in basic environments. Illustrative films include cellulose acetate phthalate, polyvinyl acetate phthalate, hydroxypropyl methylcellulose phthalate, and hydroxypropyl methylcellulose acetate succinate.

When it is desired to administer the compound as a suppository, conventional bases can be used. Illustratively, cocoa butter is a traditional suppository base. The cocoa butter can be modified by addition of waxes to raise its melting point slightly. Water-miscible suppository bases, such as polyethylene glycols of various molecular weights, can also be used in suppository formulations.

Transdermal patches can also be used to deliver the compounds. Transdermal patches can include a resinous composition in which the compound will dissolve or partially dissolve; and a film which protects the composition and which holds the resinous composition in contact with the skin. Other, more complicated patch compositions can also be used, such as those having a membrane pierced with a plurality of pores through which the drugs are pumped by osmotic action.

As one skilled in the art will also appreciate, the formulation can be prepared with materials (e.g., actives excipients, carriers (such as cyclodextrins), diluents, etc.) having properties (e.g., purity) that render the formulation suitable for administration to humans. Alternatively, the formulation can be prepared with materials having purity and/or other properties that render the formulation suitable for administration to non-human subjects, but not suitable for administration to humans.

The following list of formulations is illustrative. These illustrative formulations may be suitable for preparing pharmaceutical compositions that include the disclosed compounds as "active ingredients." The following list of formulations is illustrative and should not be interpreted as limiting the present disclosure or claims in any way:

Formulation 1
Hard gelatin capsules are prepared using the following ingredients:

|  | Quantity (mg/capsule) |
| --- | --- |
| Active Ingredient | 250 |
| Starch, dried | 200 |
| Magnesium stearate | 10 |
| Total | 460 mg |

The above ingredients are mixed and filled into hard gelatin capsules in 460 mg quantities.

Formulation 2

|  | Quantity (mg/tablet) |
| --- | --- |
| Active Ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

Formulation 3
An aerosol solution is prepared containing the following components:

|  | Weight % |
| --- | --- |
| Active Ingredient | 0.25 |
| Ethanol | 29.75 |
| Propellant 22 (chlorodifluoromethane) | 70.00 |
| Total | 100.00 |

The active compound is mixed with ethanol and the mixture added to a portion of the Propellant 22, cooled to −30° C. and transferred to a filling device. The required amount is then fed to a stainless steel container and diluted with the remainder of the propellant. The valve units are then fitted to the container.

Formulation 4
Tablets each containing 60 mg of active ingredient are made as follows:

| Active Ingredient | 60 mg |
| --- | --- |
| Starch | 45 mg |
| Microcrystalline cellulose | 35 mg |
| Polyvinylpyrrolidone | 4 mg |
| Sodium carboxymethyl starch | 4.5 mg |
| Magnesium stearate | 0.5 mg |
| Talc | 1 mg |
| Total | 150 mg |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate, and talc, previously passed through a No. 60 mesh U.S. sieve, are then added to the granules which, after mixing, are compressed on a tablet machine to yield tablets each weighing 150 mg.

Formulation 5

Capsules, each containing 80 mg medicament, are made as follows:

| Active Ingredient | 80 mg |
|---|---|
| Starch | 59 mg |
| Microcrystalline cellulose | 59 mg |
| Magnesium stearate | 2 mg |
| Total | 200 mg |

The active ingredient, cellulose, starch, and magnesium stearate are blended, passed through a No. 45 sieve, and filled into hard gelatin capsules in 200 mg quantities.

Formulation 6

Suppositories each containing 225 mg of active ingredient may be made as follows:

| Active Ingredient | 225 mg |
|---|---|
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions each containing 50 mg of medicament per 5 ml dose are made as follows:

| Active Ingredient | 50 mg |
|---|---|
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The medicament is passed through a No. 45 mesh U.S. sieve and mixed with the sodium carboxymethyl, cellulose and syrup to form a smooth paste. The benzoic acid solution, flavor, and color are diluted with some of the water and added with stirring. Sufficient water is then added to produce the required volume.

Formulation 8

An intravenous formulation containing 100 mg of medicament per 5 ml dose can be prepared as follows:

| Active Ingredient | 100 mg |
|---|---|
| Mannitol | 100 mg |
| 5N Sodium hydroxide | 200 ml |
| Purified water to total | 5 ml |

EXAMPLES

The followings Examples are illustrative only and are not intended to limit the scope of the claimed subject matter.

Example 1

Title: Discovery of 1,3,4-Oxidiazole Scaffold Compounds as Inhibitors of Superoxide Dismutase Expression Abstract The treatment of neurodegenerative diseases is difficult because of multiple etiologies and the interplay of genetics and environment as precipitating factors. In the case of amyotrophic lateral sclerosis (ALS), we have knowledge of a handful of genes that cause disease when mutated. However, drugs to counteract the effect of genetic mutations have not yet been found. One of the causative genes, Cu,Zn-superoxide dismutase (SOD1) is responsible for about 10-15% of the genetically linked autosomal dominant disease. Our rationale was that compounds that reduce expression of the mutant protein would be beneficial to slow onset and/or disease progression. We screened candidate compounds using a cell-based in vitro assay for those that reduce mutant SOD1 (G93A) protein expression. This led to the discovery of 2-[3-iodophenyl)methylsulfanyl]-5pyridin-4-yl-1,3,4-oxadiazole, a known protein kinase inhibitor that decreases G93A-SOD1 expression in vitro and in the brain and spinal cord in vivo. However, this compound has a biphasic dose response curve and a likely toxophore which limit its therapeutic window for chronic disease such as ALS. Therefore, we designed and tested a focused library of analogs for their ability to decrease SOD1 expression in vitro. This exercise resulted in the identification of a lead compound with improved drug-like characteristics and activity. Development of small molecules that reduce the expression of toxic proteins is a strategy that may also be extended to familial ALS linked to gain of function mutations in other genes.

Amyotrophic lateral sclerosis (ALS) is etiologically heterogeneous and in ten percent of cases the disease is inherited as a dominant, recessive or X-linked dominant trait, (familial ALS or FALS). The other 90 percent of cases have no history of familial disease and are called sporadic ALS or SALS. We and others have identified mutations in five genes that cause ALS. Mutations in these genes, SOD1 (1), TDP-43 (2,3), FUS (4,5), optineurin (6) (OPTN), Ubiquilin 2 (UBQLN2) (7), and C9ORF72 (8,9) cause the formation of aggregates in motor neurons of the spinal cord. Of interest is the fact that TDP-43 FUS, OPTN, and UBQLN2 are also found in inclusions in the motor neurons of SALS patients in the absence of mutations in the genes for these proteins (7,10-12). Wild-type SOD1 has been reported to be present within SALS cases with Lewy-body like inclusions (13,14) and recent reports using SOD1 aggregate specific antibodies have detected aggregated SOD1 in SALS cases (15,16) and in the cerebrospinal fluid of some ALS patients (17). One path for induction of wild-type SOD1 aggregates is through deamidation of asparagines residues (18).

There is proof of principle in SOD1-linked ALS that onset is directly influenced by the level of the mutant protein. Manipulation of SOD1 expression by gene dosage (19), siRNA (20), and neuron specific knockdown (21) is directly correlated with disease onset in vivo. Previous high-throughput screening of compound libraries for compounds that reduce SOD1 expression in cultured cells yielded compounds that were generally too toxic to use in animal studies (22). In the current work, we discovered a new class of compounds that reduce SOD1 expression in mouse fibroblasts and exhibit favorable pharmacokinetics with respect to CNS distribution. Thus, we have discovered the first non-toxic class of small molecules that may be useful for treating SOD1-FALS and SALS with involvement of SOD1.

Discovery of a New Class of SOD1 Expression Inhibitors

Figure 2:
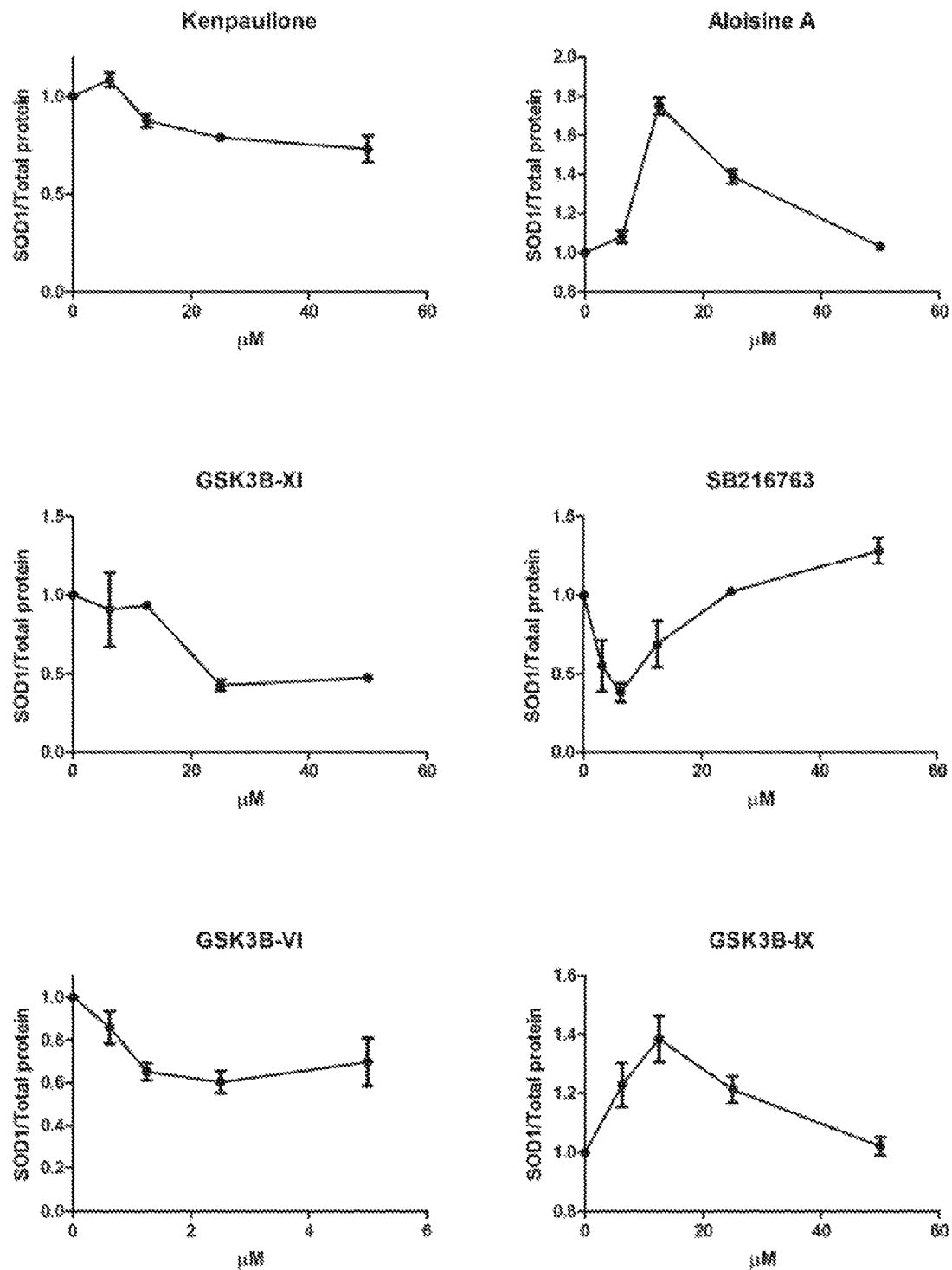
FIG. 2. Inhibition of SOD1 protein expression in fibroblasts from G93A-SOD1 mice. Fibroblasts were treated with the title compounds at the indicated concentration for 48 hr. Cells were washed, lysed, and SOD1 levels measured by ELISA. SOD1 levels are normalized to the total protein in the lysate.
Figure 3:
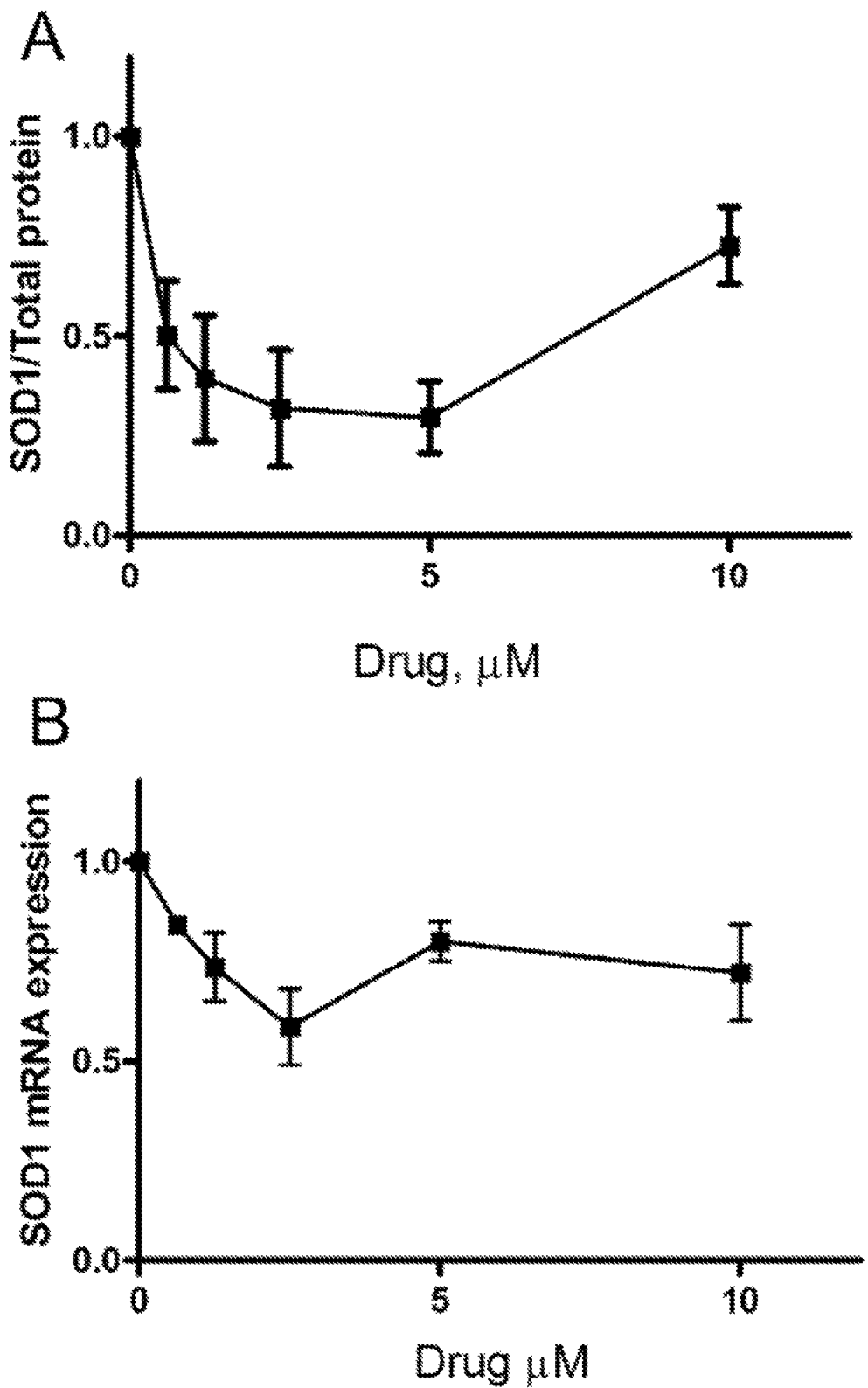
FIG. 3. Inhibition of SOD1 protein and mRNA expression by GSK3B-II in G93A-SOD1 mouse fibroblasts. A. Dose-dependent changes in G93A-SOD1 protein expression and B. SOD1 mRNA (n=3). Data are normalized to GAPDH activity (protein) or mRNA. Error bars are SEM.

Accumulated evidence suggests that inhibition of glycogen synthase kinase III (GSK3β) might be beneficial to survival of the mutant SOD1 transgenic mouse (23-25) however, SOD1 levels were not evaluated in those studies. Thus, we used cultured fibroblasts from the G93A-SOD1 transgenic mouse to screen GSK3β protein kinase inhibitors (FIG. 1) for their effects on SOD1 expression. The transgene construct contains the human SOD1 promoter so that cellular signaling processes that affect transcription of the gene will be fully functional. We chose a structurally diverse group of compounds including some natural products. FIG. 2 summarizes the results from six of the commercially available compounds. (Cell preparation and assay methods are in supplementary files). Two compounds (Aloisine A and GSK3B-IX) increased SOD1 expression, while several compounds inhibited at lower concentrations but reversed at higher concentrations yielding a biphasic pattern. Among these compounds, GSK3B-II was the most potent at inhibiting G93A-SOD1 expression (FIG. 3A). The IC$_{50}$ values for GSK3β kinase inhibition from the literature compared to SOD1 expression are in shown in Table 1.

TABLE 1

Published GSK3β inhibitors and measured SOD1 expression

| Cpd | Name | GSK3β IC50 (nM) | SOD1 IC50 (nM) | Comments |
| --- | --- | --- | --- | --- |
| 1 | GSK3B-IX | 5[b] | Increases SOD1 | Also inhibits CDK5, CDK2, CDK1 |
| 2 | GSK3B-XI | 25[b] | 10,000 | Also inhibits CDK4 |
| 3 | Kenpaullone | 23[c] | 10,000 | Also inhibits CDK5, CDK2, CDK1 |
| 4 | GSK3B-VI | 1000[d] | 650 | Covalent binding inhibitor |
| 5 | Aloisine | 650[e] | Increases SOD1 | Also inhibits CDK5, CDK1 |
| 6 | SB216763 | 9[f] | 3000 | Active against GSK3B in vivo[g] |
| 7 | GSK3B-II | 390[a] | 625 | |

[a](35);
[b]Prod. Info. Datasheet (EMD, Calbiochem);
[c](36)
[d](26);
[e](37);
[f](38);
[g](39, 40)

GSK3B-VI also inhibits SOD1 expression but this compound covalently modifies GSK3β kinase at the active site (26) and exhibits cell toxicity at concentrations greater than 5 μM making it a poor therapeutic candidate. Kenpaullone, one of the more potent GSK3β inhibitors (Table 1), only weakly decreased SOD1 expression. Thus, the disconnect between potencies of GSK3β inhibitors and their effect on SOD1 expression suggests that inhibition of GSK3β may not be the primary mechanism for decreasing G93A-SOD1 expression in cultured fibroblasts, although other explanations such as differences in cell permeability cannot be ruled out. We also determined that the decrease of SOD1 expression by GSK3B-II is primarily due to reducing the level of SOD1 mRNA (FIG. 3B). Thus, GSK3B-II affects cellular processes that lead to a decrease in the production of SOD1 mRNA and protein.

Optimization of 1,3,4-Oxidazole Inhibitors

While GSK3B-II is a potentially useful molecular probe to study the effects of reducing SOD1 expression, the compound exhibits a biphasic dose-response curve and contains a potential toxophore (Aryl-Iodo) which reduces its therapeutic potential. Hit-to-lead medicinal chemistry was undertaken to quickly expand the SAR and develop more drug-like inhibitors, especially ones without the aryl iodide group. Modifications to previously reported conditions (27, 28) were used to synthesize new 1,3,4-oxadiazole analogs as shown in Scheme 1.

Scheme1. Synthesis of 1,3,4-oxadiazole compounds. (a) hydrazine-H$_2$O, EtOH, reflux, 1 h; (b) CS$_2$, KOH, EtOH, 60° C. 18 h; (c) K$_2$CO$_3$, Aryl—Br, DMF, RT. 2 h.

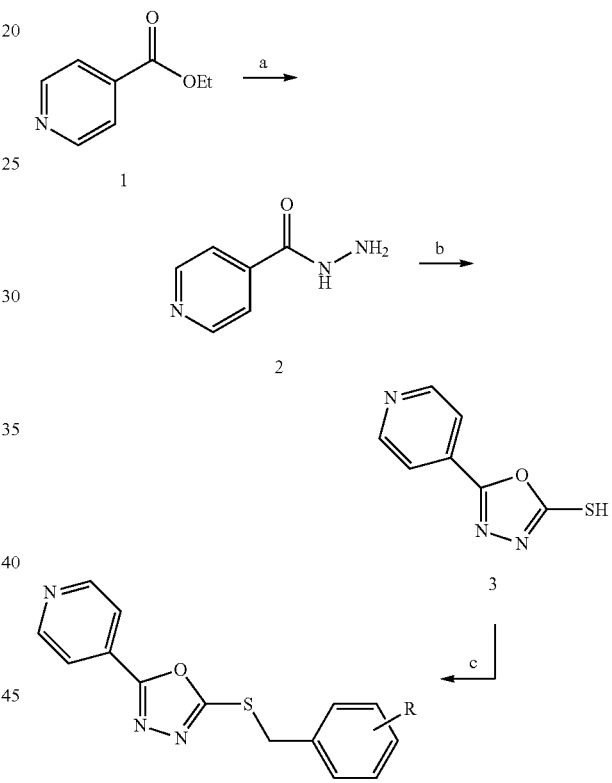

Commercially available ethyl isonicotinate was refluxed with hydrazine hydrate for 1 hr at 60° C. and the solvent was evaporated. Trituration of this solid with diethyl ether afforded pure hydrazide 2 in 86%/o yield. The treatment of hydrazide 2 with CS$_2$ and KOH in 60° C. for 18 hrs produced a solid upon concentration in vacuo. It was found that this material could be easily purified by trituration with H$_2$O followed by filtration to give thiol 3 in 78% yield, thus avoiding chromatography over the first two steps. This operationally simple procedure afforded multi-gram quantities of 3 for subsequence focused library synthesis. Finally, diversification of the aryl ring was achieved by nucleophilic displacement reaction of thiol 3 with substituted aryl bromides in room temperature DMF using K$_2$CO$_3$ as base.

The final compounds (4) were produced in yields of between 24%-74% depending on the aromatic ring substituent. All final compounds were judged to be consistent with desired product by $^1$H-NMR spectroscopy and had >95% purity as observed by liquid chromatography-mass spectrometry analysis.

Structure-activity relationships (SAR) were developed using mono aryl substituents on the benzyl ring (Table 2) to probe the requirements around this portion of the molecule.

NUCC-322 (3-pyridyl) showed either no effect on SOD1 expression or slight increases.

We sought to quantify compound behavior by Hansch analysis (29) using C log P and the sigma or sigma+ values for meta and para groups derived by Hammett (30). Sigma values are based upon the ionization of substituted benzoic acids, while the sigma+ values are based upon the solvolysis

TABLE 2

Inhibition of SOD 1 expression by 1,3,4-oxadiazoles

| ID | | ClogP$^a$ | Sigma$^b$ | Sigma+$^b$ | Relative SOD1 expression 10 μM compound (p-value)$^c$ |
|---|---|---|---|---|---|
| 7 (GSK3B-II) | X = 3-Iodo | 2.91 | 0.352 | 0.359 | 0.73 (0.022) |
| NUCC-433 | X = 3-Methoxy | 1.71 | −0.268 | 0.047 | 0.50 (0.005) |
| NUCC-319 | X = 3-Fluoro | 1.93 | 0.337 | 0.352 | 1.43 (0.001) |
| NUCC-435 | X = 4-Trifluoromethyl | 2.82 | 0.54 | 0.612 | 1.57 (0.003) |
| NUCC-439 | X = 3-Chloro | 2.51 | 0.373 | 0.399 | 0.96 |
| NUCC-432 | X = 3-Nitro | 1.53 | 0.71 | 0.674 | 1.17 |
| NUCC-318 | X = 3-Bromo | 2.65 | 0.391 | 0.405 | 0.91 |
| NUCC-434 | X = 4-Methoxy | 1.71 | 0.115 | −0.778 | 0.47 (0.001) |
| NUCC-440 | X = 4-Chloro | 2.51 | 0.227 | 0.114 | 1.23 (0.09) |
| NUCC-320 | X = 4-Bromo | 2.65 | 0.232 | 0.15 | 1.03 |
| NUCC-321 | X = 4-Iodo | 2.91 | 0.18 | 0.135 | 0.69 (0.026) |
| NUCC-324 | X = 4-Fluoro | 1.93 | 0.062 | −0.073 | 0.86 |
| NUCC-436 | X = 4-Methyl | 2.29 | −0.17 | −0.311 | 1.26 |
| NUCC-431 | X = 4-Nitro | 1.53 | 0.778 | 0.79 | 1.02 |
| NUCC-441 | X = H | 2.29 | NA | 0 | 1.33 (0.07) |

Figure 4:
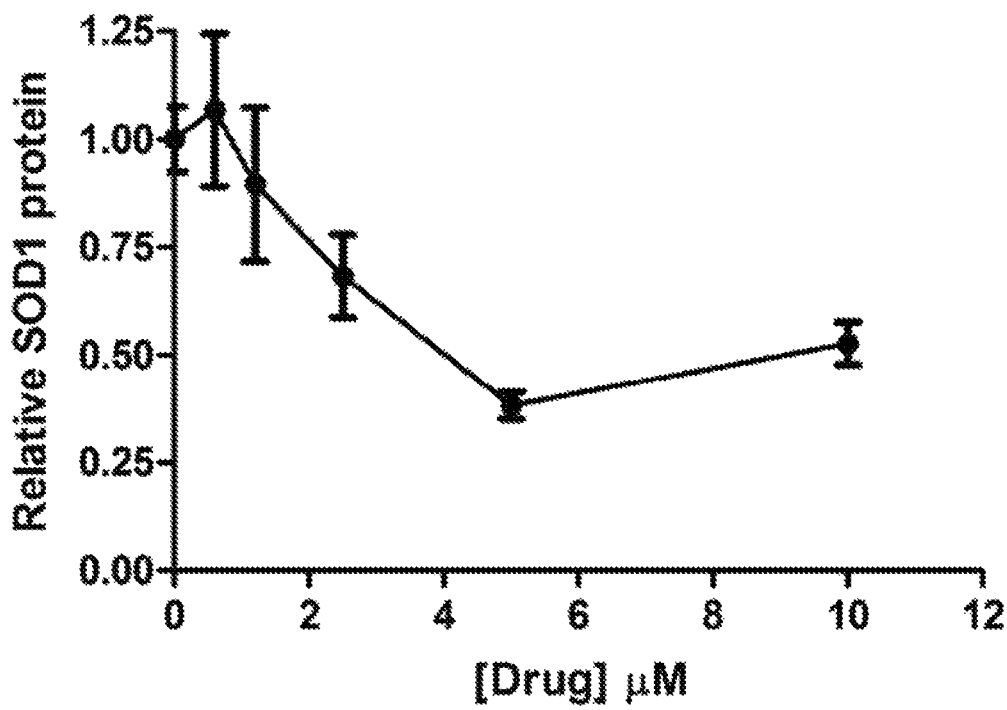
FIG. 4. Inhibition of SOD1 expression in mouse fibroblasts by NUCC-433 and NUCC-434. A. Dose-response curve for NUCC-434 and B. NUCC-433. Note the decrease in upward curvature of both compounds at 10 µM. Error bars are SEM.
Figure 4:
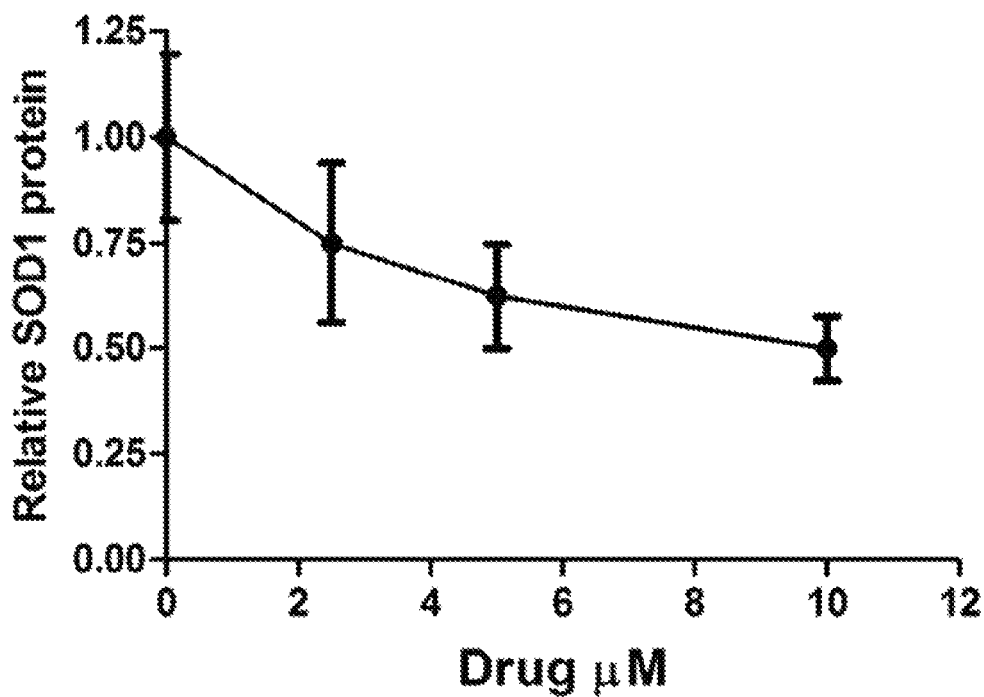

$^a$ClogP was calculated using ChemBioOffice-ChemDraw V13.
$^b$from ref (30).
$^c$If not shown Aromatic ring modifications were found to have a significant effect on the compounds' ability to reduce SOD1 expression. The two best compounds had methoxy substituents at the 3-position (NUCC-433) or 4-position (NUCC-434) and significantly reduced the level of SOD1 expression to 47-50% of control at 10 μM. Some compounds such as NUCC-319 (4-fluoro) and NUCC-435 (4-trifluromethyl) actually showed a significant increase in SOD1 expression, confirming the importance of the aryl ring in functional activity. The unsubstituted benzyl ring (NUCC-441) activates expression of SOD1 while other substituents (chloro, nitro, bromo, methyl) at the 3 or 4 position of the ring were comparable to control in SOD1 expression. Interestingly, there is a trend where electron withdrawing substituents tended to cause an increase in SOD1 expression (NUCC-319, 435, 432, 440), while electron donating groups tended to produce the largest SOD1 reduction (NUCC-433 and 434). Dose-response relationships were determined for NUCC-433 and 434 as shown in FIG. 4. Unlike GSK3B-II (FIG. 3A), both compounds exhibit a flattened rather than upward curvature at higher concentration A number of other analogs were synthesized and tested which had variations in the pyridine portion of the molecule, including the 3-hydroxyl-, 3-amino-4-pyridyl, 3-pyridyl, and fused ring system derivatives. All of these compounds with the exception of of substituted 2-phenyl-2-propyl chlorides (30). Three equations were tested for correlation of the activity data with compound parameters.

$$1-(\text{relSOD1}) = C \log P + \text{sigma} + \text{sigma+} \qquad \text{Eq1.}$$

$$1/(\text{relSOD1}) = C \log P + \text{sigma+} \qquad \text{Eq2}$$

$$1/(\text{relSOD1}) = C \log P + \text{sigma} \qquad \text{Eq 3}$$

Figure 5:
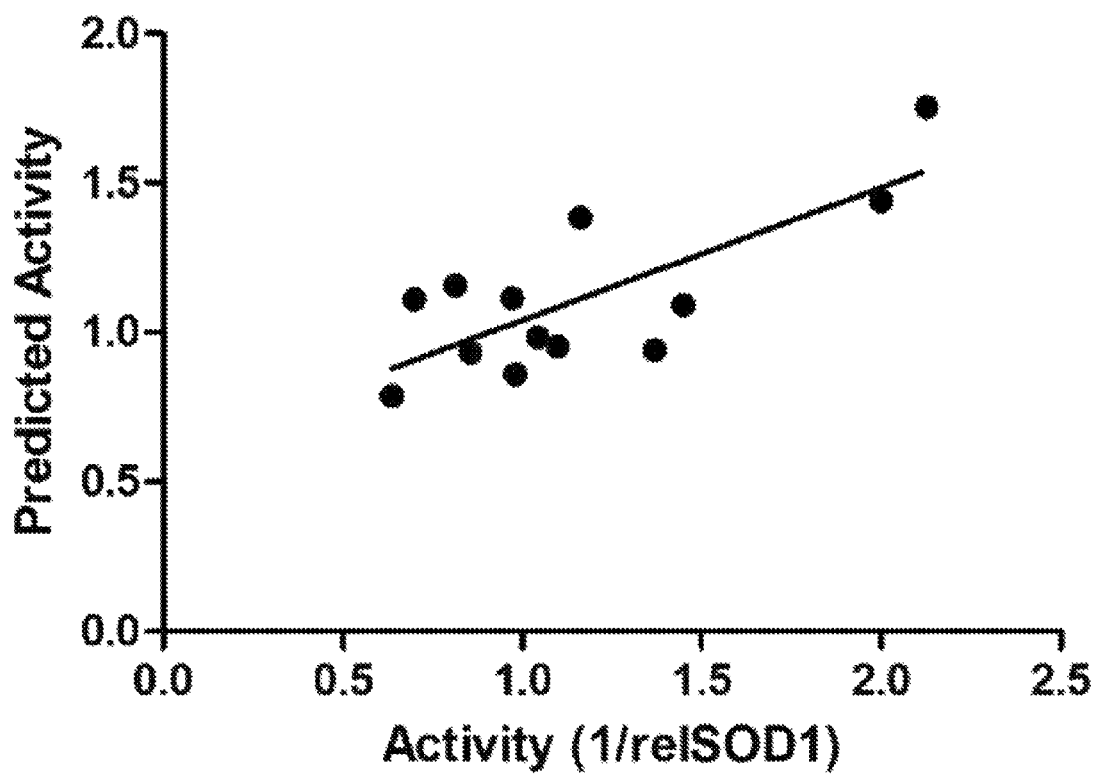
FIG. 5. Plot of predicted vs. experimental data for the inhibition of SOD1 expression by 1,3,4-oxadiazole compounds. The linear regression line was calculated using GraphPad Prism.

Using the "systemfit" (31) package in R (available at the R-project Organization's website) the coefficients for the variables were calculated by solving simultaneous equations (Ordinary Least Squares). The best fit (r2=0.58) was to Eq 1 and Eq2 (r2=0.55). The coefficients for Eq1 are: 1/relSOD1=(−0.1667)C log P+(—0.2331)sigma+(−0.4906)) sigma++1.684. A plot of the predicted and experimental values is shown in FIG. 5. The sole outlier was NUCC-436 based upon Grubbs test (available at the GraphPad website). Alternate analysis using Q values (sum of squares of the residuals) gave comparable results.

Figure 6:
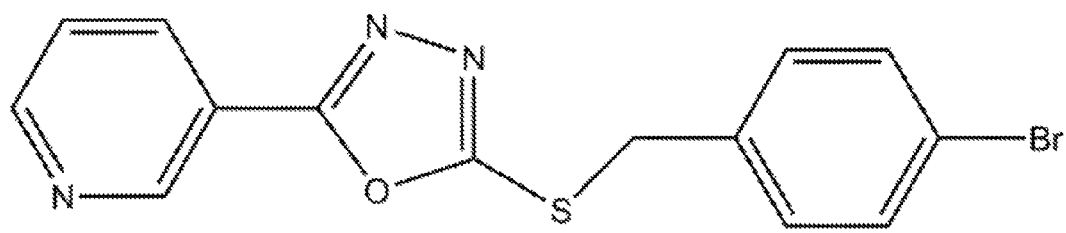
FIG. 6. Structures of related 1,3,4-oxadiazole analogs.
Figure 6:
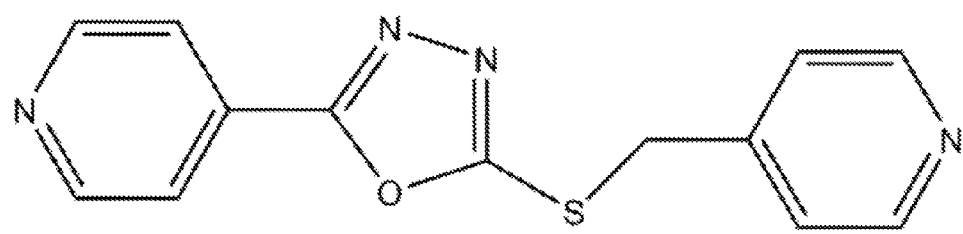
Figure 6:
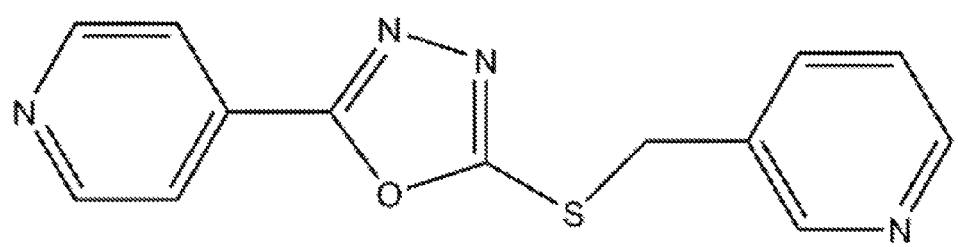

One test of the specificity of the correlation was from testing of NUCC-322 (FIG. 6), an isomer of the 4-bromo compound (NUCC-320). While NUCC-320 showed no effect on SOD1 expression, NUCC-322 inhibited SOD1 expression to 68.6% of control at 10 μM (p=0.015). This suggests that both ends of the structure contribute to target binding. Relatedly, NUCC-437 and NUCC-438 (FIG. 6) that have the benzyl group replaced by pyridyl exhibited activity (at 10 µM) not significantly different from control indicating a target preference for benzyl groups Compounds Distribute into the Mouse Brain and Spinal Cord The blood brain barrier permeability of GSK3B-II was determined in nontransgenic mice. At 20 mg/kg (intraperitoneal), the compound rapidly distributes into the brain and spinal cord. This compound is also long-lived in the CNS, with drug still detectable after 24 hrs in the brain and spinal cord (Table 3). The peak and sustained concentrations found in the spinal cord and brain indicate that the 20 mg/kg dose puts the drug into the inhibitory range found in the cellular assays.

TABLE 3

Distribution of GSK3B-II in mouse tissues after a 20 mg/kg injection (n = 2)

| Tissue | Time | Concentration (µM) |
|---|---|---|
| Brain | 1 hr | 0.944 |
| Spinal Cord | 1 hr | 4.00 |
| Serum | 1 hr | 0.672 |
| Brain | 24 hr | 0.077 |
| Spinal cord | 24 hr | 0.855 |
| Serum | 24 hr | 0.073 |

We also tested compound NUCC-434 for distribution in non-transgenic mice. However, the solubility of this compound was poor in the standard 1-2% DMSO vehicle that we used for GSKB-II. While there are a multitude of methods for improving aqueous solubility of drugs (32) we chose a relatively simple route using a cyclodextrin based carrier (Sulfo-butylether beta-cyclodextrin, Captisol) to solubilize the drug in aqueous solution. Using the cyclodextrin carrier, we were able to solubilize NUCC-434 to 2 mg/mL in water and deliver 10 mg/kg to nontransgenic mice for pharmacokinetics. Like GSK3B-II the compound entered the CNS and persisted for 24 hr in the spinal cord. However, the distribution dynamics are different in the presence of the cyclodextrin which appears to slow uptake into the CNS as the peak drug concentration was delayed (Table 4). Such changes in distribution dynamics using cyclodextrins have not been studied in detail.

TABLE 4

Distribution of CMIDD-434 in mouse tissues after a 10 mg/kg injection (n = 2)

| Time hr | Serum (µM) | Spinal Cord (µM) | Brain (µM) |
|---|---|---|---|
| 2 | 0.153 | 0.057 | 0.029 |
| 4 | 0.334 | 0.162 | 0.047 |
| 24 | 0.123 | 0.113 | ND* |

*ND = Not detected

Figure 7:
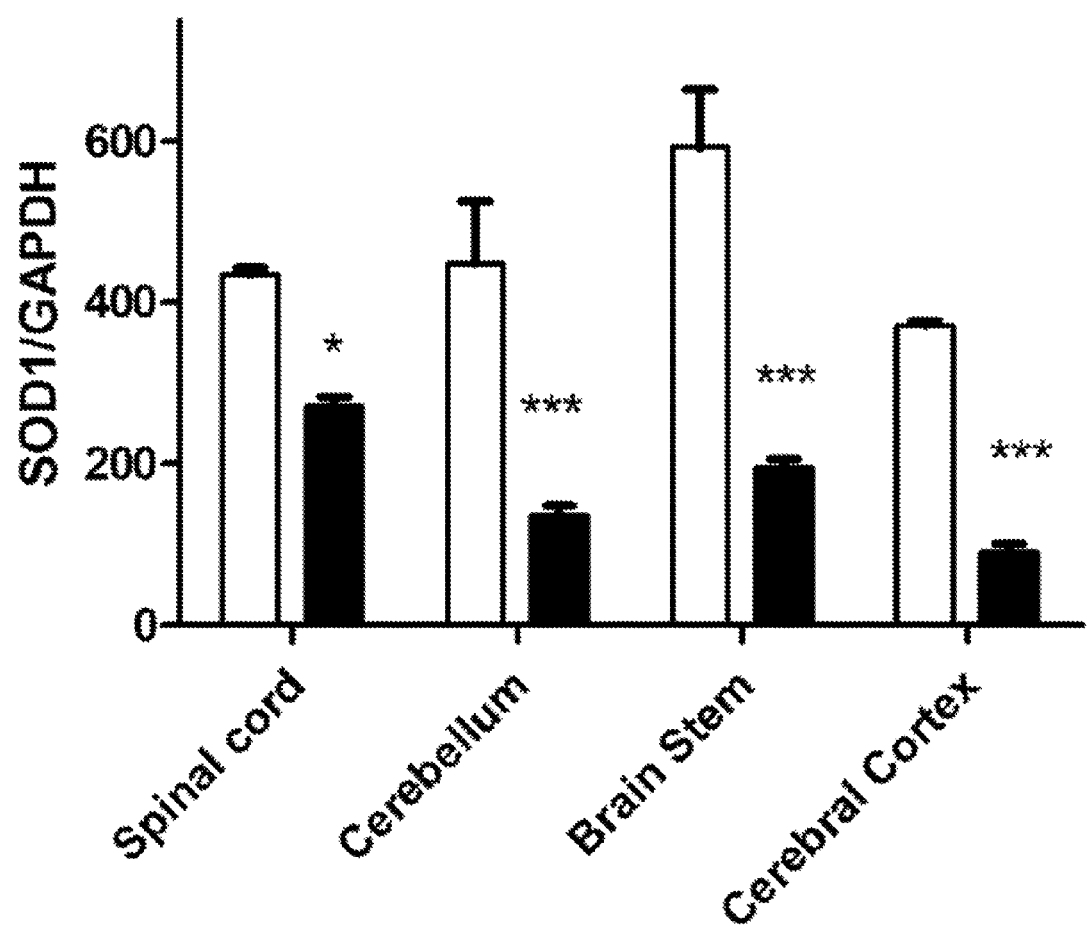
FIG. 7. Inhibition of SOD1 protein expression in the G93A-SOD1 mouse. GSK3B-I treatment was at 20 mg/kg IP every other day for 26 days. Mice were sacrificed and SOD1 measured in the indicated tissues. The change in expression was significant (*=p<0.05, ***=p<0.001) in all tested tissues (n=20). Error bars are SEM.

As a proof of concept study, compound GSK3B-II was evaluated in vivo for its ability to reduce CNS levels of SOD1. Initial testing was carried out in a small cohort (5-6 animals) of G93A-SOD1 mice (high level of mutant SOD1 expression). The drug was dosed at 20 mg/kg IP every other day for 26 days. Mice were sacrificed and SOD1 was measured by ELISA. In all tissues sampled: spinal cord, cerebellum, brain stem, and cerebral cortex, significant decreases in SOD1 were measured (FIG. 7).

Summary

Compounds GSK3B-II, NUCC-433, and NUCC-434 are the first small molecules to exhibit dose dependent reduction of SOD1 expression in vitro and in the G93A-SOD1 mouse in vivo (GSK3B-II) Compared to antisense oligonucleotides (33) and the APC analog (34), we found a comparable decrease of SOD1 protein in cultured cells with the new 1,3,4-oxdiazole analogs reported here. Thus, these and related compounds may offer an opportunity to develop a small molecule based ALS therapy.

Example 2

Title: Small Molecule Down-Regulation of SOD1 Expression

Summary

The treatment of neurodegenerative diseases is difficult because of multiple etiologies and the interplay of genetics and environment as precipitating factors. In the case of amyotrophic lateral sclerosis (ALS), a handful of genes that when are mutated cause disease. However, drugs to counteract the effect of genetic mutations have not yet been found to treat this fatal disease. One of the causative genes, Cu,Zn-superoxide dismutase (SOD1) is responsible for about 10% of the genetically linked disease. We rationalized that drugs that reduce expression of the mutant protein would be beneficial to slow onset and/or disease progression. We screened compounds using a cell-based in vitro assay and focused drug discovery on those compounds that reduce mutant SOD1 (G93A) protein expression. This lead to the discovery of GSK3B-II, a protein kinase inhibitor with neuroprotective properties, which decreases G93A-SOD1 expression in vitro and the brain and spinal cord when given to transgenic ALS model mice. This appears to be the one of the first small molecules that effectively reduces SOD1 expression without toxic side effects. The unique properties of GSK3B-II may now be exploited to develop orally active drugs that may be used to treat familial ALS caused by mutations in SOD1 and ALS cases where SOD1 contributes to pathology.

Background

Clinical trials are being carried out with two drugs that are targeted towards SOD1 downregulation/inhibition in patients with familial ALS linked to SOD1 mutations. One of these compounds, pyrimethamine, an antiparasitic compound, was reported to reduce SOD1 expression through an unknown mechanism (Lange, 2008). However, in vitro tests of pyrimethamine reported cell toxicity in the effective dose range (Wright et al., 2010). Secondly, an antisense oligonucleotide against SOD1 (ISIS SOD1 Rx) (Smith et al., 2006) is in Phase I trials as an injectable into the spinal canal. After a 28 day infusion, the antisense oligonucleotide decreases SOD1 mRNA and protein expression in the G93A-SOD1 rat brain and spinal cord by about 50% (Smith et al., 2006). Similarly, the drug extends survival in G93A-SOD1 rat by about two weeks.

Improvement Over Existing Treatments

GSK3B-II is the first small molecule compounds to exhibit dose dependent reduction of SOD1 expression in vitro and in the G93A-SOD1 mouse spinal cord and brain. Compared to antisense oligonucleotides (Smith et al., 2006) and the APC protein analog (Zhong et al., 2009) we obtained a comparable decrease of SOD1 protein in mouse tissues by administration of GSK3B-II. Thus, we believe that this compound will provide comparable results in mouse models and human trial and likely has the advantage of likely being orally active.

Description

Our lead compound, GSK3B-II has the chemical name: 2-[3-iodophenyl)methylsulfanyl]-5pyridin-4-yl-1,3,4-oxadiazole (known commercially as GSK3B-II) (FIG. 1). The compound decreases SOD1 expression in vitro in assays done in mouse fibroblasts (FIG. 3) and mouse motor neurons (FIG. 7).

GSK3B-II is a glycogen synthase kinase 3-beta (GSK3) inhibitor (IC50=390 nM). This activity is not correlated with decreasing SOD1 expression because a more potent GSK3β inhibitor such as SB216763 is not more effective at decreasing SOD1 expression in vitro. Thus, the ability to decrease SOD1 expression is not a general property of GSK3β inhibitors but rather an attribute of the structural class of compounds (1,3,4-oxadiazoles) of which GSK3B-II is a class example. Table 5 below summarizes the structure activity relationship among class members that we have developed using standard synthetic chemistry methods.

TABLE 5

| Compound Name | Compound Formula | Molecular Weight | Relative SOD1 Expression in Presence of Compound (10 µM) | Standard Deviation | P-value |
|---|---|---|---|---|---|
| NUCC-0000318 | | 348.22 | 0.902502474 | 0.268818 | 0.4949 |
| NUCC-0000319 | | 287.31 | 1.437417661 | 0.383965 | 0.01 |
| NUCC-0000320 | | 348.22 | 1.033955438 | 0.184299 | 0.7825 |
| NUCC-0000321 | | 395.22 | 0.701765619 | 0.179777 | 0.026 |
| NUCC-0000322 | | 348.22 | 0.686061164 | 0.137223 | 0.0145 |
| NUCC-0000323 | | 361.26 | 1.025833601 | 0.329468 | 0.8696 |

TABLE 5-continued
| Compound Name | Compound Formula | Molecular Weight | Relative SOD1 Expression in Presence of Compound (10 μM) | Standard Deviation | P-value |
|---|---|---|---|---|---|
| NUCC-0000324 | 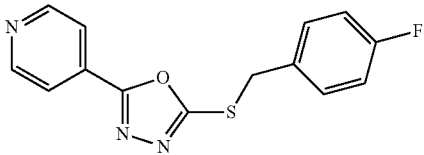 [SMILES: Fc1ccc(CSc2nnc(-c3ccncc3)o2)cc1] | 287.31 | 0.862560021 | 0.157488 | 0.2551 |
| NUCC-0000404 | 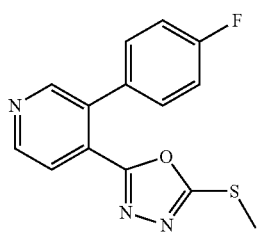 [SMILES: CSc1nnc(-c2ccncc2-c2ccc(F)cc2)o1] | 287.31 | 0.948665587 | 0.236445 | 0.702 |
| NUCC-0000405 | 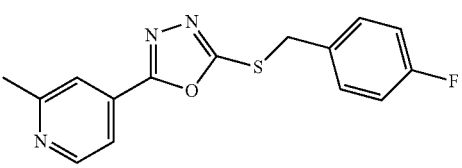 [SMILES: Cc1cc(-c2nnc(SCc3ccc(F)cc3)o2)ccn1] | 303.31 | 0.949534525 | 0.383022 | 0.77 |
| NUCC-0000406 | 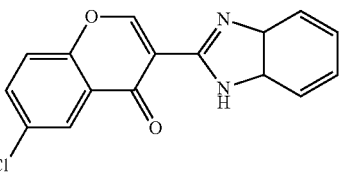 | 296.71 | 0.899003662 | 0.244281 | 0.4613 |
| NUCC-0000418 | 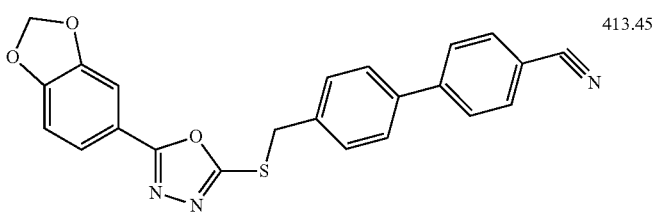 | 413.45 | 1.135580234 | 0.338367 | 0.097678 |
| NUCC-0000430 | 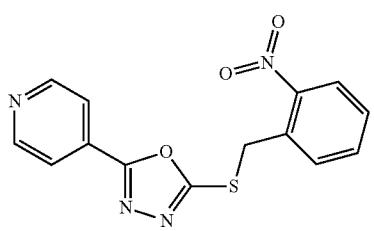 [SMILES: O=[N+]([O-])c1ccccc1CSc1nnc(-c2ccncc2)o1] | 314.32 | 1.010291338 | 0.207182 | 0.9357 |
| NUCC-0000431 | 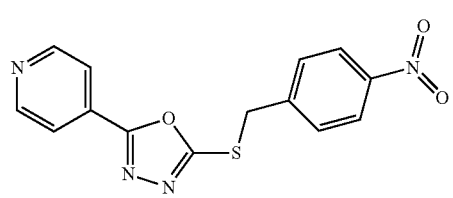 [SMILES: O=[N+]([O-])c1ccc(CSc2nnc(-c3ccncc3)o2)cc1] | 314.32 | 1.019439823 | 0.353283 | 0.9056 |

TABLE 5-continued

| Compound Name | Compound Formula | Molecular Weight | Relative SOD1 Expression in Presence of Compound (10 μM) | Standard Deviation | P-value |
|---|---|---|---|---|---|
| NUCC-0000432 | | 314.32 | 1.170792925 | 0.31447 | 0.2758 |
| NUCC-0000433 | | 299.35 | 0.499010631 | 0.130419 | 0.0005 |
| NUCC-0000434 | | 299.35 | 0.474469233 | 0.118383 | 0.0003 |
| NUCC-0000435 | | 337.32 | 1.575566215 | 0.356505 | 0.0032 |
| NUCC-0000436 | | 283.35 | 1.264971376 | 0.554189 | 0.25 |
| NUCC-0000437 | | 270.31 | 0.902523024 | 0.302842 | 0.5197 |
| NUCC-0000438 | | 270.31 | 1.116150411 | 0.40476 | 0.5188 |

TABLE 5-continued
| Compound Name | Compound Formula | Molecular Weight | Relative SOD1 Expression in Presence of Compound (10 μM) | Standard Deviation | P-value |
|---|---|---|---|---|---|
| NUCC-0000439 | 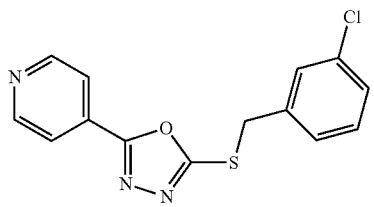 [SMILES: Clc1cccc(CSc2nnc(-c3ccncc3)o2)c1] | 303.77 | 0.958775127 | 0.258099 | 0.7671 |
| NUCC-0000440 | 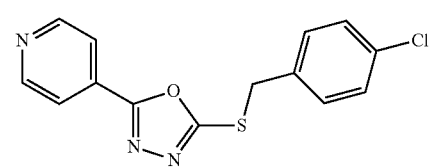 [SMILES: Clc1ccc(CSc2nnc(-c3ccncc3)o2)cc1] | 303.77 | 1.229583685 | 0.213331 | 0.091 |
| NUCC-0000441 | 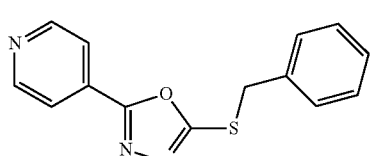 | 269.32 | 1.332857659 | 0.393499 | 0.0738 |
| NUCC-0000471 | 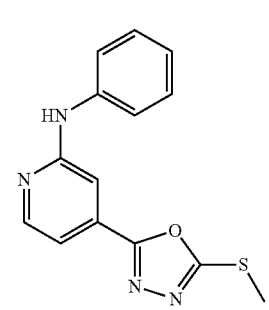 [SMILES: CSc1nnc(-c2ccnc(Nc3ccccc3)c2)o1] | 284.34 | 1.062501542 | 0.398679 | 0.724 |
| NUCC-0000472 | 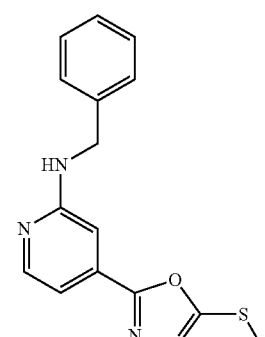 | 298.36 | 1.456738531 | 0.464612 | 0.033 |

TABLE 5-continued

| Compound Name | Compound Formula | Molecular Weight | Relative SOD1 Expression in Presence of Compound (10 μM) | Standard Deviation | P-value |
|---|---|---|---|---|---|
| NUCC-0000473 | | 292.36 | 1.270753395 | 0.362639 | 0.1201 |

GSK3B-II inhibits SOD1 expression in the G93A-SOD1 transgenic mouse motor neurons. The mechanism of inhibition is largely due to a decrease in the G93A-SOD1 mRNA. The transgene expressed in the mouse uses the native human promoter. Thus, therapy with these drugs in human subjects would also lead to a decrease in SOD1 mRNA in all tissues.

Our screen data suggests that 4-pyridyl-1,3,4-oxadiazole analogs with selected 3- or 4-benzyl ring substituents are inhibitory towards SOD1 expression. Specifically, the 3 or 4 methoxy groups as in compounds NUCC0000433 and NUCC0000434 are preferred over others.

Finally, GSK3B-II treatment of G93A-SOD1 mice shows that SOD1 protein is reduced in relevant tissues such as the spinal cord, brain stem, and cerebral cortex (FIG. 7).

Commercial Applications

The compounds synthesized and/or identified are expected to be useful in treating SOD1-linked amyotrophic lateral sclerosis and sporadic ALS in which SOD1 expression is elevated or when circulating anti-SOD1 antibodies have been detected.

REFERENCES

1. Rosen, D. R.; Siddique, T.; Patterson, D.; Figlewicz, D. A.; Sapp, P.; Hentati, A.; Donaldson, D.; Goto, J.; O'Regan, J. P.; Deng, H. X.; Nature 1993, 362(6415), 59-62.
2. Sreedharan, J.; Blair, I. P.; Tripathi, V. B.; Hu, X.; Vance, C.; Rogelj, B.; Ackerley, S.; Durnall, J. C.; Williams, K. L.; Buratti, E.; Baralle, F.; de Belleroche, J.; Mitchell, J. D.; Leigh, P. N.; Al Chalabi, A.; Miller, C. C.; Nicholson, G.; Shaw, C. E. Science 2008, 319(5870). 1668-1672.
3. Kabashi, E.; Lin, L.; Tradewell, M. L.; Dion, P. A.; Bercier, V.; Bourgouin, P.; Rochefort, D.; Bel, H. S.; Durham, H. D.; Vande, V. C.; Rouleau, G. A.; Drapeau, P. Hum. Mol. Genet. 2010, 19(4), 671-683.
4. Kwiatkowski, T. J., Jr.; Bosco, D. A.; Leclerc, A. L.; Tamrazian, E.; Vanderburg, C. R.; Russ, C.; Davis, A.; Gilchrist, J.; Kasarskis, E. J.; Munsat, T.; Valdmanis, P.; Rouleau, G. A.; Hosler, B. A.; Cortelli, P.; de Jong, P. J.; Yoshinaga, Y.; Haines, J. L.; Pericak-Vance, M. A.; Yan, J.; Ticozzi, N.; Siddique, T.; McKenna-Yasek, D.; Sapp, P. C.; Horvitz, H. R.; Landers, J. E.; Brown, R. H., Jr. Science 2009, 323(5918), 1205-1208.
5. Vance, C.; Rogelj, B.; Hortobagyi, T.; De Vos, K. J.; Nishimura, A. L.; Sreedharan, J.; Hu, X.; Smith, B.; Ruddy, D.; Wright, P.; Ganesalingam, J.; Williams, K. L.; Tripathi, V.; Al Saraj, S.; Al Chalabi, A.; Leigh, P. N.; Blair, I. P.; Nicholson, G.; de Belleroche, J.; Gallo, J. M.; Miller, C. C.; Shaw, C. E. Science 2009, 323(5918), 1208-1211.
6. van Blitterswijk, M.; van Vught, P. W.; Van Es, M. A.; Schelhaas, H. J.; van der Kooi, A. J.; de Visser, M.; Veldink, J. H.; van den Berg, L. H. Neurobiol. Aging 2011.
7. Deng, H. X.; Chen, W.; Hong, S. T.; Boycott, K. M.; Gorrie, G. H.; Siddique, N.; Yang, Y.; Fecto, F.; Shi, Y.; Zhai, H.; Jiang, H.; Hirano, M.; Rampersaud, E.; Jansen, G. H.; Donkervoort, S.; Bigio, E. H.; Brooks, B. R.; Ajroud, K.; Sufit, R. L.; Haines, J. L.; Mugnaini, E.; Pericak-Vance, M. A.; Siddique, T. Nature 2011, 477 (7363), 211-215.
8. Renton, A. E.; Majounie, E.; Waite, A.; Simon-Sanchez, J.; Rollinson, S.; Gibbs, J. R.; Schymick, J. C.; Laaksovirta, H.; van Swieten, J. C.; Myllykangas, L.; Kalimo, H.; Paetau, A.; Abramzon, Y.; Remes, A. M.; Kaganovich, A.; Scholz, S. W.; Duckworth, J.; Ding, J.; Harmer, D. W.; Hernandez, D. G.; Johnson, J. O.; Mok, K.; Ryten, M.; Trabzuni, D.; Guerreiro, R. J.; Orrell, R. W.; Neal, J.; Murray, A.; Pearson, J.; Jansen, I. E.; Sondervan, D.; Seelaar, H.; Blake, D.; Young, K.; Halliwell, N.; Callister, J. B.; Toulson, G.; Richardson, A.; Gerhard, A.; Snowden, J.; Mann, D.; Neary, D.; Nails, M. A.; Peuralinna, T.; Jansson, L.; Isoviita, V. M.; Kaivorinne, A. L.; Holtta-Vuori, M.; Ikonen, E.; Sulkava, R.; Benatar, M.; Wuu, J.; Chio, A.; Restagno, G.; Borghero, G.; Sabatelli, M.; Heckerman, D.; Rogaeva, E.; Zinman, L.; Rothstein, J. D.; Sendtner, M.; Drepper, C.; Eichler, E. E.; Alkan, C.; Abdullaev, Z.; Pack, S. D.; Dutra, A.; Pak, E.; Hardy, J.; Singleton, A.; Williams, N. M.; Heutink, P.; Pickering-Brown, S.; Morris, H. R.; Tienari, P. J.; Traynor, B. J. Neuron 2011.
9. Dejesus-Hernandez, M.; Mackenzie, I. R.; Boeve, B. F.; Boxer, A. L.; Baker, M.; Rutherford, N. J.; Nicholson, A. M.; Finch, N. A.; Flynn, H.; Adamson, J.; Kouri, N.; Wojtas, A.; Sengdy, P.; Hsiung, G. Y.; Karydas, A.; Seeley, W. W.; Josephs, K. A.; Coppola, G.; Geschwind, D. H.; Wszolek, Z. K.; Feldman, H.; Knopman, D. S.; Petersen, R. C.; Miller, B. L.; Dickson, D. W.; Boylan, K. B.; Graff-Radford, N. R.; Rademakers, R. Neuron 2011.
10. Deng, H. X.; Zhai, H.; Bigio, E. H.; Yan, J.; Fecto, F.; Ajroud, K.; Mishra, M.; Ajroud-Driss, S.; Heller, S.; Sufit, R.; Siddique, N.; Mugnaini, E.; Siddique, T. Ann. Neurol. 2010, 67(6), 739-748.
11. Mackenzie, I. R.; Bigio, E. H.; Ince, P. G.; Geser, F.; Neumann, M.; Cairns, N. J.; Kwong, L. K.; Forman, M. S.; Ravits, J.; Stewart, H.; Eisen, A.; McClusky, L.; Kretzschmar, H. A.; Monoranu, C. M.; Highley, J. R.; Kirby, J.; Siddique, T.; Shaw, P. J.; Lee, V. M.; Trojanowski, J. Q. Ann. Neurol. 2007, 61(5), 427-434.
12. Maruyama, H.; Morino, H.; Ito, H.; Izumi, Y.; Kato, H.; Watanabe, Y.; Kinoshita, Y.; Kamada, M.; Nodera, H.; Suzuki, H.; Komure, O.; Matsuura, S.; Kobatake, K.; Morimoto, N.; Abe, K.; Suzuki, N.; Aoki, M.; Kawata, A.; Hirai, T.; Kato, T.; Ogasawara, K.; Hirano, A.: Takumi, T.; Kusaka, H.; Hagiwara, K.; Kaji, R.; Kawakami, H. Nature 2010, 465(7295), 223-226.
13. Shibata, N.; Hirano, A.; Kobayashi, M.; Sasaki, S.; Kato, T.; Matsumoto, S.; Shiozawa, Z.; Komori, T.; Ikemoto, A.; Umahara, T.; Neurosci. Lett. 1994, 179(1-2), 149-152.
14. Matsumoto, S.; Kusaka, H.; Ito, H.; Shibata, N.; Asayama, T.; Imai, T. Clin. Neuropathol. 1996, 15(1), 41-46.
15. Bosco, D. A.; Morfini, G.; Karabacak, N. M.; Song, Y.; Gros-Louis, F.; Pasinelli, P.; Goolsby, H.; Fontaine, B. A.; Lemay, N.; McKenna-Yasek, D.; Frosch, M. P.; Agar, J. N.; Julien, J. P.; Brady, S. T.; Brown, R. H., Jr. Nat. Neurosci. 2010, 13(11), 1396-1403.
16. Forsberg, K.; Jonsson, P. A.; Andersen, P. M.; Bergemalm, D.; Graffmo, K. S.; Hultdin, M.; Jacobsson, J.; Rosquist, R.; Marklund, S. L.; Brannstrom, T. PLoS. One. 2010, 5(7), e11552.
17. Zetterstrom, P.; Andersen, P. M.; Brannstrom, T.; Marklund, S. L. J. Neurochem. 2011, 117(1), 91-99.
18. Shi, Y.; Rhodes, N. R.; Abdolvahabi, A.; Kohn, T.; Cook, N. P.; Marti, A. A.; Shaw, B. F. J. Am. Chem. Soc. 2013, in press.
19. Deng, H. X.; Siddique, T. Arch. Neurol. 2000, 57(12), 1695-1702.
20. Ralph, G. S.; Radcliffe, P. A.; Day, D. M.; Carthy, J. M.; Leroux, M. A.; Lee, D. C.; Wong, L. F.; Bilsland, L. G.; Greensmith, L.; Kingsman, S. M.; Mitrophanous, K. A.; Mazarakis, N. D.; Azzouz, M. Nat. Med. 2005, 11(4), 429-433.
21. Wang, L.; Grisotti, G.; Roos, R. P. J. Neurochem. 2010, 113(1), 166-174.
22. Broom, W. J.; Auwarter, K. E.; Ni, J.; Russel, D. E.; Yeh, L. A.; Maxwell, M. M.; Glicksman, M.; Kazantsev, A. G.; Brown, R. H., Jr. J. Biomol. Screen. 2006, 11(7), 729-735.
23. Koh, S. H.; Lee, Y. B.; Kim, K. S.; Kim, H. J.; Kim, M.; Lee, Y. J.; Kim, J.; Lee, K. W.; Kim, S. H. Eur. J. Neurosci. 2005, 22(2), 301-309.
24. Koh, S. H.; Kim, Y.; Kim, H. Y.; Hwang, S.; Lee, C. H.; Kim, S. H. Exp. Neurol. 2007, 205(2), 336-346.
25. Yang, Y. M.; Gupta, S. K.; Kim, K. J.; Powers, B. E.; Cerqueira, A.; Wainger, B. J.; Ngo, H. D.; Rosowski, K. A.; Schein, P. A.; Ackeifi, C. A.; Arvanites, A. C.; Davidow, L. S.; Woolf. C. J.; Rubin, L. L. Cell Stem Cell 2013, 12(6), 713-726.
26. Perez, D. I.; Conde, S.; Perez, C.; Gil, C.; Simon, D.; Wandosell, F.; Moreno, F. J.; Gelpi, J. L.; Luque, F. J.; Martinez, A. Bioorg. Med. Chem. 2009, 17(19), 6914-6925.
27. Ahmad, R.; Iqbal, R.; Akhtar, H.; Zia, u. H.; Duddeck, H.; Stefaniak, L.; Sitkowski, J. Nucleosides Nucleotides Nucleic Acids 2001, 20(9), 1671-1682.
28. Lo, M. F.; Kramer, T.; Gu, J.; Anumala, U. R.; Marinelli, L.; La, P., V; Novellino, E.; Franco, B.; Demedts, D.; van Leuven, F.; Fuertes, A.; Dominguez, J. M.; Plotkin, B.; Eldar-Finkelman, H.; Schmidt, B. J. Med. Chem. 2012, 55(9), 4407-4424.
29. Kurup, A.; Garg, R.; Hansch, C. Chem. Rev. 2001, 101(8), 2573-2600.
30. Leffler, J. E.; Grunwald, E. Rates and Equilibria of Organic Reactions; Wiley: New York, 1963.
31. Journal of Statistical Software 2007, 23(4), 1-40.
32. Williams, H. D.; Trevaskis, N. L.; Charman, S. A.; Shanker, R. M.; Charman, W. N.; Pouton, C. W.; Porter, C. J. Pharmacol. Rev. 2013, 65(1), 315-499.
33. Smith, R. A.; Miller, T. M.; Yamanaka, K.; Monia, B. P.; Condon, T. P.; Hung, G.; Lobsiger, C. S.; Ward, C. M.; McAlonis-Downes, M.; Wei, H.; Wancewicz, E. V.; Bennett, C. F.; Cleveland, D. W. J. Clin. Invest 2006, 116(8), 2290-2296.
34. Zhong, Z.; Ilieva, H.; Hallagan, L.; Bell, R.; Singh, I.; Paquette, N.; Thiyagarajan, M.; Deane, R.; Fernandez, J. A.; Lane, S.; Zlokovic, A. B.; Liu, T.; Griffin, J. H.; Chow, N.; Castellino, F. J.; Stojanovic, K.; Cleveland, D. W.; Zlokovic, B. V. J. Clin. Invest 2009, 119(11), 3437-3449.
35. Naerum, L.; Norskov-Lauritsen, L.; Olesen, P. H. Bioorg. Med. Chem. Lett. 2002, 12(11), 1525-1528.
36. Leost, M.; Schultz, C.; Link. A.; Wu, Y. Z.; Biernat, J.; Mandelkow, E. M.; Bibb, J. A.; Snyder, G. L.; Greengard, P.; Zaharevitz, D. W.; Gussio, R.; Senderowicz, A. M.; Sausville, E. A.; Kunick, C.; Meijer, L. Eur. J. Biochem. 2000, 267(19), 5983-5994.
37. Mettey, Y.; Gompel, M.; Thomas, V.; Garnier, M.; Leost, M.; Ceballos-Picot, I.; Noble, M.; Endicott, J.; Vierfond, J. M.; Meijer, L. J. Med. Chem. 2003, 46(2), 222-236.
38. Coghlan, M. P.; Culbert, A. A.; Cross, D. A.; Corcoran, S. L.; Yates, J. W.; Pearce, N. J.; Rausch, O. L.; Murphy, G. J.; Carter, P. S.; Roxbee, C. L.; Mills, D.; Brown, M. J.; Haigh, D.; Ward, R. W.; Smith, D. G.; Murray, K. J.; Reith, A. D.; Holder, J. C. Chem. Biol. 2000, 7(10), 793-803.
39. Valerio, A.; Bertolotti, P.; Delbarba, A.; Perego, C.; Dossena, M.; Ragni, M.; Spano, P.; Carruba, M. O.; De Simoni, M. G.; Nisoli, E. J. Neurochem. 2011, 116(6), 1148-1159.
40. Min, W. W.; Yuskaitis, C. J.; Yan, Q.; Sikorski, C.; Chen, S.; Jope, R. S.; Bauchwitz, R. P. Neuropharmacology 2009, 56(2), 463-472.
41. Lange, D. J. Pyrimethamine as a therapy for SOD1 associated FALS: Early Findings. Amyotroph. Lateral. Scler. 9[Suppl. 1], 45-47. 2008.
42. Wright, P. D., Huang, M., Weiss, A., Matthews, J., Wightman, N., Glicksman, M., and Brown, R. H., Jr. (2010). Screening for inhibitors of the SOD1 gene promoter: pyrimethamine does not reduce SOD1 levels in cell and animal models. Neurosci. Lett. 482, 188-192.

It will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

We claim:

1. A method for treating a disease or disorder that is associated with elevated SOD1 expression or activity in a patient in need thereof, the method comprising administering to the patient an effective amount of the following compound for reducing SOD1 expression or activity:

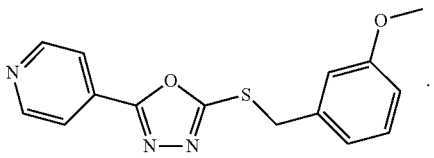 [SMILES: COc1cccc(CSc2nnc(-c3ccncc3)o2)c1]

2. The method of claim 1, wherein the disease or disorder is a neurological disease or disorder.

3. The method of claim 2, wherein the neurological disease or disorder is a degenerative neurological disease or disorder.

4. The method of claim 3, wherein the degenerative neurological disease or disorder is amyotrophic lateral sclerosis (ALS).

5. A method for treating a disease or disorder that is associated with elevated SOD1 expression or activity in a patient in need thereof, the method comprising administering to the patient an effective amount of the following compound for reducing SOD1 expression or activity:

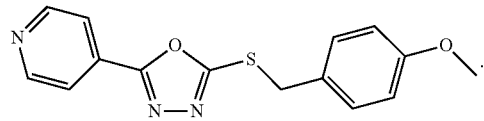 [SMILES: COc1ccc(CSc2nnc(-c3ccncc3)o2)cc1]

6. The method of claim 5, wherein the disease or disorder is a neurological disease or disorder.

7. The method of claim 6, wherein the neurological disease or disorder is a degenerative neurological disease or disorder.

8. The method of claim 7, wherein the degenerative neurological disease or disorder is amyotrophic lateral sclerosis (ALS).

* * * * *